United States Patent
Benson

(10) Patent No.: US 11,078,481 B1
(45) Date of Patent: Aug. 3, 2021

(54) METHODS FOR SCREENING FOR CANCER TARGETS

(71) Applicant: KSQ Therapeutics, Inc., Cambridge, MA (US)

(72) Inventor: Micah Benson, Cambridge, MA (US)

(73) Assignee: KSQ Therapeutics, Inc., Cambridge, MA (US)

(*) Notice: Subject to any disclaimer, the term of this patent is extended or adjusted under 35 U.S.C. 154(b) by 192 days.

(21) Appl. No.: 15/668,652

(22) Filed: Aug. 3, 2017

Related U.S. Application Data

(60) Provisional application No. 62/370,560, filed on Aug. 3, 2016.

(51) Int. Cl.
| | |
|---|---|
| *C40B 30/04* | (2006.01) |
| *C12N 15/10* | (2006.01) |
| *C07K 14/715* | (2006.01) |
| *C07K 14/705* | (2006.01) |
| *C07K 16/28* | (2006.01) |
| *C12N 5/09* | (2010.01) |
| *C12N 9/22* | (2006.01) |
| *C12N 5/0783* | (2010.01) |

(52) U.S. Cl.
CPC .... *C12N 15/1086* (2013.01); *C07K 14/70596* (2013.01); *C07K 14/7153* (2013.01); *C07K 16/2863* (2013.01); *C07K 16/2896* (2013.01); *C12N 5/0636* (2013.01); *C12N 5/0693* (2013.01); *C12N 9/22* (2013.01); *C12N 2501/2302* (2013.01); *C12N 2501/53* (2013.01); *C12N 2501/599* (2013.01); *C12N 2502/1114* (2013.01); *C12N 2502/30* (2013.01); *C40B 30/04* (2013.01)

(58) Field of Classification Search
None
See application file for complete search history.

(56) References Cited

U.S. PATENT DOCUMENTS

| | | | |
|---|---|---|---|
| 8,546,553 | B2 | 10/2013 | Terns et al. |
| 8,697,359 | B1 | 4/2014 | Zhang et al. |
| 8,771,945 | B1 | 7/2014 | Zhang et al. |
| 8,795,965 | B2 | 8/2014 | Zhang et al. |
| 8,865,406 | B2 | 10/2014 | Zhang et al. |
| 8,871,445 | B2 | 10/2014 | Cong et al. |
| 8,889,356 | B2 | 11/2014 | Zhang et al. |
| 8,889,418 | B2 | 11/2014 | Zhang et al. |
| 8,895,308 | B1 | 11/2014 | Zhang et al. |

(Continued)

FOREIGN PATENT DOCUMENTS

| | | |
|---|---|---|
| WO | WO 2007/025097 A2 | 3/2007 |
| WO | WO 2008/021207 A2 | 2/2008 |

(Continued)

OTHER PUBLICATIONS

Parnas et al (Cell, 2015. vol. 162, pp. 675-686).*

(Continued)

*Primary Examiner* — Christian C Boesen
(74) *Attorney, Agent, or Firm* — Wolf, Greenfield & Sacks, P.C.

(57) ABSTRACT

This invention describes a novel CRISPR/Cas9 target identification platform permitting the discovery of novel genes and pathways involved in the ability of T cells and NK cells to react against and generate an anti-tumor response.

16 Claims, 11 Drawing Sheets

(56) References Cited

U.S. PATENT DOCUMENTS

| | | |
|---|---|---|
| 8,906,616 B2 | 12/2014 | Zhang et al. |
| 8,906,682 B2 | 12/2014 | June et al. |
| 8,932,814 B2 | 1/2015 | Cong et al. |
| 8,945,839 B2 | 2/2015 | Zhang et al. |
| 8,993,233 B2 | 3/2015 | Zhang et al. |
| 8,999,641 B2 | 4/2015 | Zhang et al. |
| 9,637,739 B2 | 5/2017 | Virginijus et al. |
| 9,790,490 B2 | 10/2017 | Zhang et al. |
| 9,822,372 B2 | 11/2017 | Zhang et al. |
| 9,834,791 B2 | 12/2017 | Zhang et al. |
| 9,840,713 B2 | 12/2017 | Zhang et al. |
| 9,855,297 B2 | 1/2018 | Duchateau et al. |
| 9,890,393 B2 | 2/2018 | Duchateau et al. |
| 2010/0076057 A1 | 3/2010 | Sontheimer et al. |
| 2010/0093617 A1 | 4/2010 | Barrangou et al. |
| 2010/0257638 A1 | 10/2010 | Cai et al. |
| 2011/0217739 A1 | 9/2011 | Terns et al. |
| 2011/0300538 A1 | 12/2011 | Barrangou et al. |
| 2012/0149115 A1 | 6/2012 | Kim et al. |
| 2012/0277120 A1 | 11/2012 | Serber et al. |
| 2013/0011828 A1 | 1/2013 | Barrangou et al. |
| 2013/0288251 A1 | 10/2013 | Horvath et al. |
| 2014/0068797 A1 | 3/2014 | Doudna et al. |
| 2014/0179770 A1 | 6/2014 | Zhang et al. |
| 2014/0186843 A1 | 7/2014 | Zhang et al. |
| 2014/0186916 A1 | 7/2014 | Allen et al. |
| 2014/0189896 A1 | 7/2014 | Zhang et al. |
| 2014/0242664 A1 | 8/2014 | Zhang et al. |
| 2014/0242699 A1 | 8/2014 | Zhang et al. |
| 2014/0273230 A1 | 9/2014 | Chen et al. |
| 2014/0273233 A1 | 9/2014 | Chen et al. |
| 2014/0310830 A1 | 10/2014 | Zhang et al. |
| 2014/0357530 A1 | 12/2014 | Zhang et al. |
| 2015/0020223 A1 | 1/2015 | Zhang et al. |
| 2015/0031134 A1 | 1/2015 | Zhang et al. |
| 2015/0058069 A1 | 2/2015 | Chavda et al. |
| 2015/0184139 A1 | 7/2015 | Zhang et al. |
| 2015/0203872 A1 | 7/2015 | Zhang et al. |
| 2015/0240261 A1 | 8/2015 | Siksnys et al. |
| 2015/0284727 A1 | 10/2015 | Kim et al. |
| 2015/0291961 A1 | 10/2015 | Siksnys et al. |
| 2015/0322457 A1 | 11/2015 | Kim et al. |
| 2015/0344912 A1 | 12/2015 | Kim et al. |
| 2016/0017366 A1 | 1/2016 | Chen et al. |
| 2016/0046961 A1 | 2/2016 | Jinek et al. |
| 2016/0060653 A1 | 3/2016 | Doudna et al. |
| 2016/0060654 A1 | 3/2016 | Doudna et al. |
| 2016/0068864 A1 | 3/2016 | Doudna et al. |
| 2016/0102324 A1 | 4/2016 | Duchateau et al. |
| 2016/0115488 A1 | 4/2016 | Zhang et al. |
| 2016/0115489 A1 | 4/2016 | Zhang et al. |
| 2016/0120905 A1 | 5/2016 | Galetto et al. |
| 2016/0122774 A1 | 5/2016 | Duchateau et al. |
| 2016/0130608 A1 | 5/2016 | Doudna et al. |
| 2016/0130609 A1 | 5/2016 | Doudna et al. |
| 2016/0138008 A1 | 5/2016 | Doudna et al. |
| 2016/0145645 A1 | 5/2016 | Bahr et al. |
| 2016/0184362 A1 | 6/2016 | Duchateau et al. |
| 2016/0272965 A1* | 9/2016 | Zhang ............... C12N 15/1082 |
| 2016/0272999 A1 | 9/2016 | Duchateau et al. |
| 2016/0281072 A1 | 9/2016 | Zhang et al. |
| 2016/0298096 A1 | 10/2016 | Charpentier et al. |
| 2016/0340662 A1 | 11/2016 | Zhang et al. |
| 2017/0016025 A1 | 1/2017 | Poirot et al. |
| 2017/0051310 A1 | 2/2017 | Doudna et al. |
| 2017/0051312 A1 | 2/2017 | Jinek et al. |
| 2017/0051354 A1 | 2/2017 | Davis et al. |
| 2017/0107536 A1 | 4/2017 | Zhang et al. |
| 2017/0152528 A1 | 6/2017 | Zhang et al. |
| 2017/0166893 A1 | 6/2017 | Doudna et al. |
| 2017/0175142 A1 | 6/2017 | Zhang et al. |
| 2017/0191078 A1 | 7/2017 | Zhang et al. |
| 2017/0191123 A1 | 7/2017 | Kim et al. |
| 2018/0187149 A1* | 7/2018 | Ma .................... C07K 14/7051 |

FOREIGN PATENT DOCUMENTS

| | | |
|---|---|---|
| WO | WO 2010/011961 A2 | 1/2010 |
| WO | WO 2010/054108 A2 | 5/2010 |
| WO | WO 2010/054154 A2 | 5/2010 |
| WO | WO 2012/054726 A1 | 4/2012 |
| WO | WO 2012/149470 A1 | 11/2012 |
| WO | WO 2012/164565 A1 | 12/2012 |
| WO | WO 2013/098244 A1 | 7/2013 |
| WO | WO 2013/126794 A1 | 8/2013 |
| WO | WO 2013/141680 A1 | 9/2013 |
| WO | WO 2013/142578 A1 | 9/2013 |
| WO | WO 2013/176772 A1 | 11/2013 |
| WO | WO 2014/089290 A1 | 6/2014 |
| WO | WO 2014/093661 A2 | 6/2014 |
| WO | WO 2014/093701 A1 | 6/2014 |
| WO | WO 2014/093718 A1 | 6/2014 |
| WO | WO 2014/191128 A1 | 12/2014 |
| WO | WO 2014/191518 A1 | 12/2014 |
| WO | WO 2014/191521 A2 | 12/2014 |
| WO | WO 2014/204727 A1 | 12/2014 |
| WO | WO 2014/205192 A2 | 12/2014 |
| WO | WO 2015/071474 A2 | 5/2015 |
| WO | WO 2015/075175 A1 | 5/2015 |
| WO | WO 2015/075195 A1 | 5/2015 |
| WO | WO 2015/089351 A1 | 6/2015 |
| WO | WO 2015/089427 A1 | 6/2015 |
| WO | WO 2015/155341 A1 | 10/2015 |
| WO | WO 2015/161276 A2 | 10/2015 |
| WO | WO 2015/167959 A1 | 11/2015 |
| WO | WO 2016/094872 A1 | 6/2016 |
| WO | WO 2016/094874 A1 | 6/2016 |
| WO | WO 2016/094880 A1 | 6/2016 |
| WO | WO 2016/100974 A1 | 6/2016 |
| WO | WO 2016/205613 A1 | 12/2016 |
| WO | WO 2016/210271 A1 | 12/2016 |
| WO | WO 2017/053762 A1 | 3/2017 |
| WO | WO 2017/079673 A1 | 5/2017 |
| WO | WO 2017/120546 A1 | 7/2017 |
| WO | WO 2017/123609 A1 | 7/2017 |
| WO | WO 2017/209809 A1 | 12/2017 |
| WO | WO 2018/035387 A1 | 2/2018 |
| WO | WO 2018/035388 A1 | 2/2018 |

OTHER PUBLICATIONS

Chavez et al., "Comparison of Cas9 activators in multiple species." Nature Methods (2016); 13(7): 563-567.

Cleary et al., "Production of complex nucleic acid libraries using highly parallel in situ oligonucleotide synthesis." Nature Methods (2004); 1(3): 241-247.

Cooper et al., "Highly efficient large-scale lentiviral vector concentration by tandem tangential flow filtration." Journal of Virological Methods (2011); 177(1): 1-9.

Davis et al., "Small molecule-triggered Cas9 protein with improved genome-editing specificity." Nature Chemical Biology (2015); 11(5): 316-318.

Doench et al., "Optimized sgRNA design to maximize activity and minimize off-target effects of CRISPR-Cas9." Nature Biotechnology (2016); 34: 184-191.

Doench et al., "Rational design of highly active sgRNAs for CRISPR-Cas9-mediated gene inactivation." Nature Biotechnology (2014); 32(12): 1262-1267.

Dominguez et al., "Beyond editing: repurposing CRISPR-Cas9 for precision genome regulation and interrogation." Nature Reviews Molecular Cell Biology (2016); 17(1): 5-15.

Dow et al., "Inducible in vivo genome editing with CRISPR-Cas9." Nature Biotechnology (2015); 33: 390-394.

Geraerts et al., "Upscaling of lentiviral vector production by tangential flow filtration." The Journal of Gene Medicine (2005); 7(10): 1299-1310.

Gilbert et al., "Genome-Scale CRISPR-Mediated Control of Gene Repression and Activation." Cell (2014); 159(3): 647-661.

(56) References Cited

OTHER PUBLICATIONS

Henriksen et al., "Comparison of RNAi efficiency mediated by tetracycline-responsive H1 and U6 promoter variants in mammalian cell lines." Nucleic Acids Research (2007); 35(9): e67.

Jiang et al., "An optimized method for high-titer lentivirus preparations without ultracentrifugation." Scientific Reports (2015); 5: 13875.

Konermann et al., "Genome-scale transcriptional activation by an engineered CRISPR-Cas9 complex." Nature (2015); 517(7536): 583-588.

Ma et al., "A CRISPR-Based Screen Identifies Genes Essential for West-Nile-Virus-Induced Cell Death." Cell Reports (2015); 12(4): 673-683.

Moreno-Mateos et al., "CRISPRscan: designing highly efficient sgRNAs for CRISPR-Cas9 targeting in vivo." Nature Methods (2015); 12(10): 982-988.

Rey-Giraud et al., "In Vitro Generation of Monocyte-Derived Macrophages under Serum-Free Conditions Improves Their Tumor Promoting Functions." PLoS ONE (2012); 7(8): e42656.

Schumann et al., "Generation of knock-in primary human T cells using Cas9 ribonucleoproteins." PNAS (2015); 112(33): 10437-10442.

Sternberg and Doudna, "Expanding the Biologist's Toolkit with CRISPR-Cas9." Molecular Cell (2015); 58(4): 568-574.

Tiscornia et al., "Production and purification of lentiviral vectors." Nature Protocols (2006); 1(1): 241-245.

Wang et al., "Genetic Screens in Human Cells Using the CRISPR-Cas9 System." Science (2014); 343(6166): 80-84.

Wang et al., "Identification and characterization of essential genes in the human genome." Science (2015); 350(6264): 1096-1101.

Wucherpfennig et al., "Genetic screens to study the immune system in cancer." Current Opinion in Immunology (2016); 41:55-61.

Zhang et al., "A CRISPR screen defines a signal peptide processing pathway required by flaviviruses." Nature (2016); 535(7610): 164-168.

Zhang et al., "A more efficient RNAi inducible system for tight regulation of gene expression in mammalian cells and xenograft animals." RNA (2007); 13: 1375-1383.

\* cited by examiner

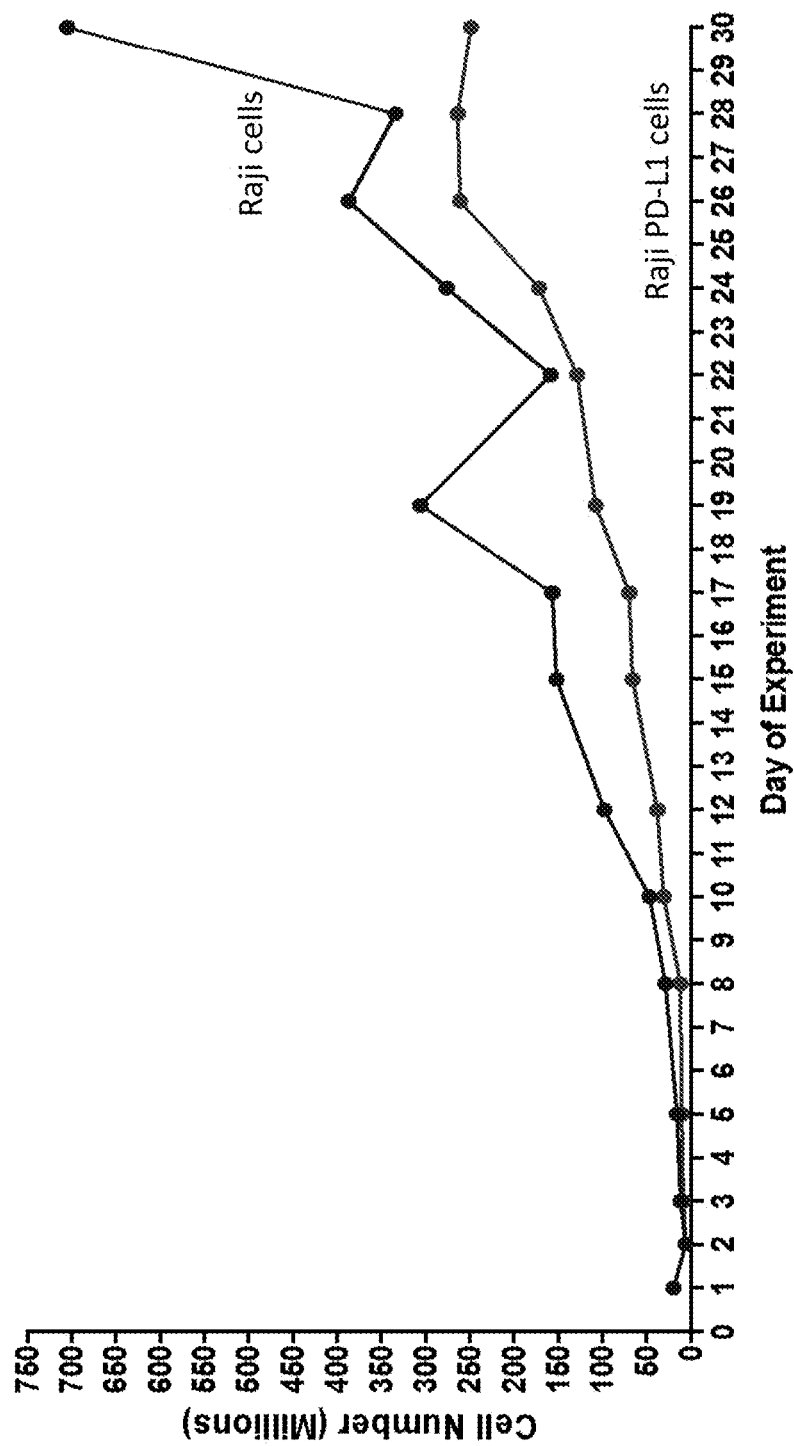

US 11,078,481 B1

METHODS FOR SCREENING FOR CANCER TARGETS

REFERENCE TO RELATED APPLICATIONS

This application claims priority to U.S. Provisional Patent Application No. 62/370,560, filed Aug. 3, 2016, the contents of which are incorporated herein by reference in its entirety.

FIELD OF THE INVENTION

The present invention relates to methods and materials useful in screening for and discovery of novel genes and pathways that are involved in the ability of T cells, NK, NKT cells and other cells to react against the presence of tumors and antigen-presenting cells and generate an anti-tumor response. The methods described herein provide enhanced ability to identify novel targets and/or interrogate validated targets and pathways involved in cellular processes by screening the activity of genes, proteins and small molecules, and can thereby help to accelerate discovery and development of oncology therapies.

BACKGROUND OF THE INVENTION

Nucleic acid libraries have been constructed using biologically derived or chemically synthesized nucleic acids as substrates. Methods have been developed for the purpose of generating complex, and hence, comprehensive, libraries which are useful for functional analysis of genomes. For example, Cleary et al. (2004) Nature Methods 1: 241-247 discloses complex libraries of defined nucleic acids developed in order to create large-scale libraries of short hairpin RNAs (shRNAs) targeting numerous human and mouse genes.

In the past decade, use of clustered regularly interspaced short palindromic repeats (CRISPR) gene editing technology has sparked a revolution in the biological sciences. CRISPR site-specific editing in eukaryotic cells has been used for the modification of many plant and animal models. Sternberg and Doudna (2015) Molecular Cell 58: 568-574, describe the development and use of CRISPR-Cas9 for such diverse applications as genome editing, gene regulation, and genome-wide screening systems.

T cells have been engineered to express chimeric antigen receptors (CARs), wherein the engineered T cells exhibit an antitumor property. For example, U.S. Pat. No. 8,906,682 describes CAR-T cells which have been engineered to comprise an extracellular domain having an antigen binding domain (such as a domain that binds to CD19), fused to an intracellular signaling domain of the T cell antigen receptor complex zeta chain (such as CD3F). When expressed in the T cell, the CAR is able to redirect antigen recognition based on the antigen binding specificity. In the case of CD19, the antigen is expressed on malignant B cells. CAR-T cells are currently being used in over 100 clinical trials in a wide range of oncology indications.

SUMMARY OF THE INVENTION

The present invention provides a novel target identification platform permitting the discovery of novel genes and pathways involved in the ability of T cells, NK cells, NKT cells, and other immune cells to react against and generate an anti-tumor response. Specifically, CRISPR/Cas9 screens can be performed on T cells, NK cells, NKT cells, antigen presenting cells of the lymphoid lineage, cells of myeloid lineage, and tumor cells, in both an in vitro and in vivo setting. Prior to this invention, conducting subgenome-scale and genome-wide CRISPR/Cas9 screens using human cells was prohibitive given the challenges associated with obtaining a monoclonal population of T cells reactive to a tumor antigen with which to conduct the CRISPR/Cas9 screens. In addition, screens assessing multiple different tumor types by the same population of T cells were nearly impossible.

In some embodiments, methods are provided for obtaining T cells that are resistant to tumor suppression or deactivation. In some embodiments, the method includes obtaining a population of tumor cells that express an extracellular protein target and a population of T cells that express a chimeric antigen receptor (CAR). In some embodiments, the CAR comprises an intracellular signaling domain and an extracellular target binding domain that binds to the extracellular target that is expression on the tumor cell population. In some embodiments, the CAR-T cells have been further transduced with Cas9 and with a gRNA library capable of selectively editing the CAR-T cells at one or more locations of the CAR-T genome to form a subpopulation of edited CAR-T cells. In some embodiments, the method includes co-culturing the subpopulation of edited CAR-T cells with the population of tumor cells. In some embodiments, the co-culture is done for at least seven days. In some embodiments, after co-culturing edited CAR-T cells that accumulate over the co-culture period are isolated. In some embodiments, the CAR-T cells that are isolated have been edited in such a manner as to make the CAR-T cells resistant to tumor suppression or deactivation.

In a further embodiment, methods are provided for identifying tumor cells that are resistant to inhibition by T cells. In some embodiment, the method includes obtaining a population of tumor cells that express an extracellular target and that have been engineered to express a Cas9 protein and a guide RNA library that is capable of selectively editing the population of tumor cells at one or more sites within the tumor cell genome to form a subpopulation of edited tumor cells. In some embodiments the method also includes obtaining a population of T cells that express a CAR comprising an intracellular signaling domain and an extracellular target-binding domain that binds to the extracellular protein target expressed by the tumor cells. In some embodiments, the method includes co-culturing the subpopulation of CAR-T cells with the subpopulation of edited tumor cells and isolating those edited tumor cells that accumulate over the co-culture period. In some embodiments, the co-culture period is at least 7 days. In some embodiments, the isolated tumor cells that accumulate over the co-culture period have been edited to make the tumor cells resistant to inhibition by T cells.

In some embodiments, a method is provided for obtaining NK cells or NKT cells that are resistant to tumor suppression or deactivation. In some embodiments, the method includes obtaining a population of tumor cells that express an extra cellular protein target and a population of NK cells or NKT cells that express a CAR comprising an intracellular signaling domain and an extracellular target-binding domain that binds to the extracellular protein target expressed on the population of tumor cells. In some embodiments, the CAR-NK cells or CAR-NKT cells have been further transduced with Cas9 and a guide RNA library that is capable of selectively editing the CAR-NK cells or CAR-NKT cells in one or more locations of the CAR-NK cell genome or the CAR-NKT cell genome to form a subpopulation of edited CAR-NK cells or CAR-NKT cells. In some embodiments, the method further includes co-culturing the subpopulation of CAR-NK cells or edited CAR-NKT cells of with the population of tumor cells. In some embodiments, the co-culturing period is at least 7 days. In some embodiments, the method includes isolating those edited CAR-NK cells or edited CAR-NKT cells that accumulate over the co-culture period. In some embodiments, the isolated CAR-NK cells or CAR-NKT cells that accumulate over the co-culture period have been edited in such a manner as to make them resistant to suppression or deactivation by the tumor cells.

In some embodiments, a method is provided for identifying tumor cells that are resistant to inhibition of NK cells or NKT cells. In some embodiments, the method includes obtaining a population of tumor cells that express an extracellular protein target and have been engineered to express a Cas9 protein and a gRNA library that is capable of selectively editing the population of tumor cells at one or more sites within the tumor cell genome to form a subpopulation of edited tumor cells. In some embodiments, the method further includes obtaining a population of NK cells or NKT cells that express a CAR that comprises an intracellular signaling domain and an extracellular target-binding domain that binds to the extracellular protein target expressed by the tumor cells. In some embodiments, the method also includes co-culturing the subpopulation of edited tumor cells with the subpopulation of CAR-NK cells or CAR-NKT cells. In some embodiments, the co-culture period is at least 7 days. In some embodiments, the method also includes isolating those edited tumor cells that accumulate over the co-culture period. In some embodiments, those edited tumor cells that accumulate over the co-culture period have been edited in such a manner as to make the edited tumor cells resistant to inhibition by NK cells or NKT cells.

In some embodiments, a method is provided for obtaining T cells that are resistant to suppression or deactivation by antigen presenting cells (APC). In some embodiments, the method includes obtaining a population of APC that express an extracellular protein target and a population of T cells that express a CAR that comprises an intracellular signaling domain and an extracellular target-binding domain that binds to the extracellular protein target expressed by such APC to form a population of CAR-T cells that express the extracellular target-binding protein on their surface. In some embodiments, the CAR-T cells have been further transduced with Cas9 and a gRNA library that is capable of selectively editing CAR-T cells at one or more locations of the CAR-T cell genome to form subpopulation of APC. In some embodiments, the method includes co-culturing the subpopulation of edited CAR-T cells with the population of APCs and isolating those CAR-T cells that accumulate over the culture period. In some embodiments, the co-culture period is at least 7 days. In some embodiments, the isolated CAR-T cells that accumulate over the culture period have been edited in a manner as to make the CAR-T cells resistant to suppression or deactivation by said APC.

In some embodiments, a method is provided for identifying antigen presenting cells that are resistant to inhibition by T cells. In some embodiments, the method includes obtaining a population of APC that express an extracellular protein target and that have been further modified to express a Cas9 protein and a gRNA library that is capable of selectively editing the population of APC at one or more sites within the APC genome to form a subpopulation of edited APC. In some embodiments, the method further includes obtaining a population of T cells that express a CAR comprising an intracellular signaling domain and an extracellular target-binding domain that binds to the extracellular protein target expressed on the APC. In some embodiments, the method includes co-culturing the subpopulation of CAR-T cells with the subpopulation of edited APC and isolating the edited APC that accumulate over the co-culture period. In some embodiments, the co-culture period is at least 7 days. In some embodiments, the edited APC that accumulate over the co-culture period have been edited in such a manner as to make them resistant to inhibition by T cells.

In some embodiments, a method is provided for obtaining NK cells or NKT cells that are resistant to suppression or deactivation by antigen presenting cells. In some embodiments, the method includes obtaining a population of APC that express an extracellular protein target and a population of NK cells or NKT cells that express a CAR comprising an intracellular signaling domain and an extracellular target binding domain that binds to the extracellular protein target expressed on the APC. In some embodiments, the CAR-NK cells or CAR-NKT cells have been further transduced to express Cas9 and a gRNA library that is capable of selectively editing the CAR-NK cells or CAR-NKT cells at one or more locations in the CAR-NK cell genome or CAR-NKT cells genome to form a subpopulation of edited CAR-NK cells or edited CAR-NKT cells. In some embodiments, the method includes co-culturing the APC with the subpopulation of edited CAR-NK cells or CAR-NKT cells and isolating those edited CAR-NK cells or CAR-NKT cells that accumulate over the co-culture period. In some embodiments, the co-culture period is at least 7 days. In some embodiments, the CAR-NK cells or CAR-NKT cells that accumulate over the co-culture period have been edited in such a way as to make them resistant to suppression or deactivation by the APC.

In some embodiments, a method is provided for identifying APC that are resistant to inhibition by NK cells or NKT cells. In some embodiments, the method includes obtaining a population of APC that express an extracellular protein target and that have been further engineered to express a Cas9 protein and a gRNA library that is capable of selectively editing the population of APC at one or more sites within the APC genome to form a subpopulation of edited APC. In some embodiments, the method also includes obtaining a population of NK cells or NKT cells that express a CAR comprising an intracellular signaling domain and an extracellular target-binding domain that binds to the extracellular protein target expressed on the APC to form a subpopulation of CAR-NK or CAR-NKT cells that express the extracellular target-binding protein on their surface. In some embodiments, the method further includes co-culturing the subpopulation of CAR-NK cells or CAR-NKT cells with the subpopulation of edited APC and isolating the edited APC that accumulate over the co-culture period. In some embodiments, the co-culture period is at least 7 days. In some embodiments, the edited APC that accumulate over the co-culture period have been edited in such a way as to make them resistant to inhibition by NK cells or NKT cells.

In some embodiments, the extracellular protein target on the APC or tumor cells is naturally expressed in the population of APC or tumor cells. In other embodiments, the extracellular protein target is not naturally expressed in the population of ACP or the expression is augmented such that the ACP or tumor cells have been engineered to express the extracellular protein target. In some embodiments, the extracellular protein target is HER2, EGFR, ERBB2, ERBB3, ERBB4; CD19; or CD20.

In some embodiments, the cells that have been engineered or transduced to express Cas9 have been engineered or transduced with a nucleic acid that encodes for Cas9. In some embodiments, the nucleic acid encodes Cas9 is mRNA. In some embodiments, the mRNA that encodes Cas9 is introduced into the cell via electroporation. In some embodiments, the nucleic acid expressing Cas9 is a viral vector. In some embodiments, the viral vector is a lentiviral vector and is introduced at a titer of at least about $1 \times 10^6$ or at least about $1 \times 10^7$ infectious particles/mL. In some embodiments the Cas9 is a dCas9. In some embodiments the dCas9 is fused with a repressor domain. In some embodiments the repressor domain is MAX-interacting protein 1 (MXI1), Krüppel-associated box (KRAB) domain or four concatenated mSin3 domains (SID4X). In some embodiments, the dCas9 is fused with a transcriptional activator. In some embodiments, the transcriptional activator is one or multiple repeats of the herpes simplex VP16 activation domain (VP64 or VP160) or the nuclear factor-κB (NF-κB) transactivating subunit activation domain (p65AD). In some embodiments the Cas9 protein comprises a single chain d-Cas9-VP64 fusion protein. In some embodiments, the nucleic acid encoding Cas9 further encodes a selectable marker. In some embodiments, the selectable marker is a fluorophore or an antibiotic resistance gene.

BRIEF DESCRIPTION OF THE FIGURES

FIG. 7A-FIG. 7B shows growth curves of CAR-T cells engineered to lack endogenous TCR expression and to contain a guide library targeting ~6,000 genes with 10 guides per genes.

DETAILED DESCRIPTION OF THE INVENTION

Figure 1:
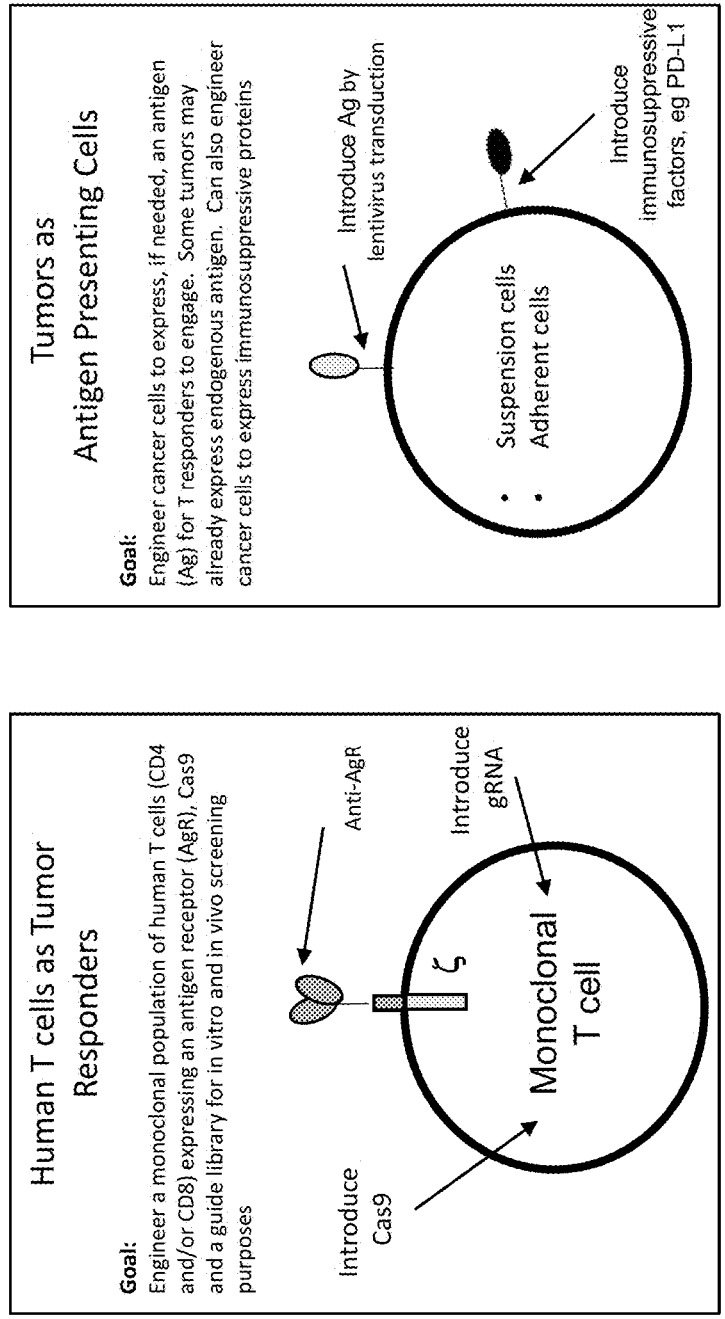
FIG. 1 illustrates aspects of the invention in which a monoclonal population of human T cells (e.g., CD4 and/or CD8) are engineered to express a chimeric antigen receptor. The extracellular domain of the CAR may comprise a single chain fragment of an antibody variable domain (scFv) that will target a protein expressed (naturally or by cell engineering) on the cell surface of tumors or APCs.

In some embodiments, the present invention provides a method of identifying genes that modulate tumor-mediated immune suppression of effector cells, such as T cells, NK cells, and/or NKT cells. In general, the methods described herein comprise co-culture of (i) activator cells that have been engineered to express a known protein antigen, and optionally have been further engineered to express a protein involved in immune suppression; and (ii) receptor-engineered cells (RE-cells) that have been engineered to express an antigen receptor specific for the known protein antigen, a Cas9 nuclease, and a library of guide RNAs. The activator cells and gene-edited RE-cells are then co-cultured for a pre-determined amount of time and RE-cells that are resistant to immune suppression mechanisms will remain active and proliferate. Sequencing of the RE-cells thereby identifies the relative enrichment of a particular guide RNA, or group of guide RNAs, and allows for identification of genes and/or pathways that mediate or are associated with resistance to tumor-cell mediated immune suppression.

In some embodiments, the RE-T cells engineered to express Cas9 and a library of guide RNA allows for screening to identify novel genes involved in the ability of T cells to react to a tumor cell or antigen-presenting cell expressing a target antigen. In some embodiments, the activator cell (e.g., the tumor cell, or APC) can be further engineered to express Cas9 and a library of guide RNAs in a manner that allows for screening to identify novel genes and pathways involved in the ability of tumor cells to evade recognition and destruction by immune effector cells.

As used herein, the use of the word "a" or "an" when used in conjunction with the term "comprising" in the claims and/or the specification may mean "one," but is also consistent with the meaning of "one or more," "at least one," and "one or more than one."

Receptor Engineered Cells (RE-Cells)

In some embodiments, immune effector cells (e.g., T cells, NK cells, and/or NKT cells) are engineered to express an antigen receptor that is specific to a protein target expressed by the activator cells. Such cells are referred to herein as "receptor-engineered cells" or "RE-cells" and may refer to cells (e.g., T cells, NK cells, or the like) that have been engineered to express an antigen-specific receptor that is able to bind to a protein target. Thus, for example, the term 'RE-T cells' includes cells engineered to express a chimeric antigen receptor (CAR) and cells engineered to express a TCR.

Cell types that are useful in the present invention and may be engineered as RE-cells include cells involved in mounting the innate and adaptive immune responses, including but not limited to thymocytes, lymphocytes, such as T-cells, B-cells, natural killer (NK) cells, and NKT cells, macrophages, monocytes, eosinophils, basophils, neutrophils, dendritic cells, and mast cells. In certain embodiments, the RE-cell described herein are T cells, NK cells, or NKT cells. In particular embodiments, the RE-cells described herein are T cells. In certain embodiments, the T cells are $CD4^+$ T cells. In certain embodiments, the T cells are $CD8^+$ T cells. The methods described herein can similarly be practiced using NK cells and NKT cells (e.g., RE-NK cells can be prepared, including CAR-NK cells and TCR-NK cells).

To obtain human T cells, NK cells, NKT cells or T regulatory cells, Ficoll density centrifugation can be performed on peripheral blood obtained from human donors, with buffy coats containing purified PBMCs harvested. T cells or other desired responder cell types can be purified from the buffy coat by means known in the art, including the use of the EasySep Human T Cell Enrichment Kit (StemCell Technologies, Vancouver BC, Canada). Other potential sources of primary human responder cells include leukopaks obtained by apheresis, cord blood, tumor infiltrating lymphocytes (TILs) from tumors, and surgically resected thymus.

In some embodiments, the cells are mammalian cells. In some embodiments the cells are human cells. In certain embodiments, the cells are human T cells. In some embodiments, the RE-cells are primary cells, such as primary human T cells. In some embodiments, the RE-cells are derived from cells lines.

In some embodiments, receptor-engineered cells (RE-cells) are engineered to express an antigen receptor. In some embodiments, the antigen receptor is a chimeric antigen receptor (CAR). In such embodiments, the RE-cells may be referred to as "CAR-NK cells," "CAR-NKT cells," or "CAR-T cells," depending on the cell type. In particular embodiments, the RE-cells described herein are CAR-T cells. In general, CARs comprise an intracellular domain comprising a signaling domain. In some embodiments, the intracellular signaling domain may be derived from the T cell antigen receptor complex zeta chain (such as CD3ξ signaling domains). Additional signaling domains useful in the present invention include the signaling domains of FcγRIII and FcεRI, and the T-lymphocyte activation domain. In some embodiments, the CARs may further comprise a costimulatory domain on the intracellular and cytoplasmic domain. In some embodiments, the co-stimulatory domain may be derived from 4-1BB, CD28, CD40, MyD88, and/or CD70. The intracellular domain of the CAR is then fused to an extracellular domain that is designed to bind to a protein target expressed on the surface of a target cell, such as a tumor cell or an antigen presenting cell (APC). The extracellular domain of a CAR may comprise an antigen binding fragment derived from an antibody. Antigen binding domains that are useful in the present invention include, for example: scFvs; receptors; antibodies; binding elements; antigen binding regions of antibodies; variable regions of the heavy/light chains; and single chain antibodies.

In certain embodiments of the invention, transgenic or engineered T cell receptors (TCRs) may be used in place of CARs. In such embodiments, the RE-cells may be referred to as "TCR-T cells," "TCR-NK cells," or "TCR-NKT cells," depending on the cell type. In such embodiments, recombinant TCRs directed against peptides derived from tumor-relevant antigens, such as hTERT, pg100, MART1, HPV 16-E7, NY-ESO or MAGE-A10, are introduced to cells, in the place of a CAR.

In some embodiments, the RE-cells described herein may be engineered to express an antigen-specific receptor (i.e. a CAR or a TCR) directed against a relevant tumor antigen, or fragments or epitopes thereof. In some embodiments, the relevant tumor antigen is Human Epidermal Growth Factor Receptor 2 (HER2), receptor tyrosine-protein kinases Erb-B2, 3, and/or 4 (ERBB2, ERBB3, ERBB4), CD19, CD20, CD5, CD7, CD10, CD22, CD30, CD33 (CD33/IL3Ra), CD34, CD38, CD41, CD44, CD49f, CD56, CD74, CD123, CD133, CD138, CD171, antigen of a cytomegalovirus (CMV) infected cell (e.g., a cell surface antigen), epithelial glycoprotein2 (EGP2), epithelial glycoprotein-40 (EGP-40), epithelial cell adhesion molecule (EpCAM), folate-binding protein (FBP), fetal acetylcholine receptor (AChR), folate receptor-α, Ganglioside G2 (GD2), Ganglioside G3 (GD3), human telomerase reverse transcriptase (hTERT), interleukin-13 receptor subunit alpha-2 (IL-13R-α2), kappa-light chain, kinase insert domain receptor (KDR), Lewis A (CA19.9), Lewis Y (LeY), L1 cell adhesion molecule (L1-CAM), melanoma antigen family A1 (MAGE-AI), MAGEA3, Mucin 16 (Muc-16), Mucin 1 (Muc-1), Mesothelin (MSLN), NKG2D ligands, cancer-testis antigen NY-ESO-1, oncofetal antigens (e.g., h5T4), prostate stem cell antigen (PSCA), prostate-specific membrane antigen (PSMA), tumor-associated glycoprotein 72 (TAG-72), vascular endothelial growth factor R2 (VEGF-R2), and Wilms tumor protein (WT-1), ROR1, c-Met, Glycolipid F77, EGFRvIII, TCR; carbonic anhydrase IX (CAIX), carcinoembryonic antigen (CEA), tumor associated glycoprotein 72 (TAG72); GP100; MART1; p53; BCMA or CS-1.

In certain embodiments, the present invention provides methods for producing a polyclonal population of primary receptor-engineered immune cells further comprising a Cas9 protein and a guide RNA library that are suitable for performing a genome wide screen against cancer cell lines expressing cognate antigens. In some embodiments, RE-cells in which recombinant TCRs or CARs have been introduced are further engineered to express a Cas9 protein and a guide RNA library capable of editing one or more gene loci in the RE-cell to generate a population of edited RE-cells. In particular embodiments, the edited RE-cell is an edited CAR-T cell. In certain embodiments, the edited RE-cells are primary immune cells. In certain embodiments, the edited RE-cells are primary human T cells. In some embodiments, the edited RE-cells described herein (e.g., edited CAR-T cells) comprise a gRNA targeting a gene encoding a component of the endogenous TCR complex, such as genes encoding the TCRa chain (e.g., TRAC) and/or TCR chain. In such embodiments the edited RE-cells do not express an endogenous TCR on their cell surface. In some embodiments, the edited RE-cells comprise a gRNA targeting a gene encoding a component of the endogenous TCR complex and a gRNA library. In some embodiments, the edited RE-cells comprise a gRNA targeting the TRAC gene and a gRNA library Activator Cells In some embodiments, activator cells (e.g., tumor cells or antigen-presenting cells (APC)) may be engineered to express a known protein target, such as a known tumor antigen. In further embodiments, activator cells are further engineered to express a cell surface protein known to be involved in immune suppression, such as an immune checkpoint protein. The extracellular protein target can be expressed on any tumor cell type or antigen presenting cell (APC), making the screening system described herein adaptable to any tumor or APC amenable to engineering for expression of the protein target. In certain embodiments, the tumor cells or APCs may naturally express the extracellular protein target against which the RE-T cells are engineered, for example, an antigen such as HER2 or ERBB2. In this instance, CRISPR/Cas9 screens can be performed without the need to engineer the tumor cell or APC to express a chimeric or non-natural protein antigen. The target may comprise a naturally occurring tumor antigen (such as CD19, CD20, HER2, EGFR), or may be an antigenic protein target that is introduced into the cell and expressed on the cell surface (FIG. 1).

In some embodiments, tumor cells, either solid or liquid in origin, are transduced and engineered to express an antigen (Ag) against which T cells recognize and react. In some embodiments, tumor cells expressing Ag can be enriched under selection, or, if necessary, cloned by single-cell sorting. In some embodiments, the activator cells (e.g., tumor cells or APCs) can be further engineered to express additional immunosuppressive molecules, for example, PD-L1, in order to obtain tumor cells that express both Ag and an immunosuppressive molecule in a tightly-controlled manner.

In some embodiments, the tumor cells or APCs may naturally express a protein target on its surface. For example, a tumor cell or APC may naturally express a target protein such as CD19, CD20, HER2 or EGFR. Alternatively, the tumor or APC may be engineered to express an antigenic protein target on its surface. In certain embodiments, the tumor or APC may be engineered to express an antigenic protein target that is derived from another cell type, that is, a tumor antigen that is not otherwise endogenously expressed on the tumor cell or APC, or an immunosuppressive molecule.

Many cell types can be used as activators of the RE-cells described herein (e.g., CAR-T cells or TCR-T cells). Exemplary cell types that may be used as activator cells include tumor cells and antigen-presenting cell (APC) subsets such as monocytes, macrophages, granulocytes, and dendritic cells. In some embodiments, the activator cells are obtained directly from human donors (e.g., primary cells). In some embodiments, patient-derived tumors, in particular, those that express Her2/ERBB2, can be obtained directly from human patients. To obtain human primary APCs for CRISPR/Cas9 screening, peripheral blood mononuclear cells (PBMCs) can be obtained from peripheral blood obtained from human donors, with PBMC buffy coats harvested by Ficoll density gradient centrifugation. Primary cells can also be obtained from bone marrow aspirates, cord blood, or directly from tumors during surgical resection. APC subsets can be further purified using commercially available magnetic bead enrichment kits (e.g., kits available from StemCell Technologies). To obtain primary human macrophages and dendritic cell subsets, purified monocytes can be differentiated into each subset using established in vitro protocols wherein cytokine cocktails, such as IL-4 and GM-CSF for dendritic cells and M-CSF or GM-CSF for macrophages, drive differentiation (Rey-Giraud et al., Plos One, 2012). In some embodiments, macrophages can be skewed to represent an M1 or an M2 phenotype by further in vitro conditioning with cytokines such as IFNγ in combination with LPS for M1, or IL-4 and IL-10 for M2 macrophages.

In some embodiments, the activator cells are derived from cell lines. Tumor cell lines, including RAJI and DLD1 cells, can be obtained from ATCC (Manassas, Va.) or other commercial vendors, and can be engineered if necessary, as in the case of DLD1 cells, to express tCD19. In cell lines and patient-derived tumor cells that do not express detectable levels of CD19, cells can be engineered by lentiviral transduction to express the tCD19 protein. In addition, APC cell lines are commercially available from vendors such as ATCC.

Expression of Protein Targets

In some embodiments, the activator cells described herein may not endogenously express the required protein recognized by the RE-cells described herein. In such embodiments, in order to render the RE-cells capable of recognizing an activator cell, the activator cell can be engineered to express a protein antigen recognized by the antigen receptor expressed on the RE-cells. Introduction of exogenous proteins and/or nucleic acids to produce the RE-cells and/or the activator cells described herein may be achieved by any means known in the art, including viral transduction (e.g., lentiviral transduction), plasmid transfection, or mRNA transfection, for example by electroporation.

Protein targets that are suitable for expression on the activator cells described herein (e.g., tumor cells or APCs) include cancer/tumor specific antigens, such as Human Epidermal Growth Factor Receptor 2 (HER2), receptor tyrosine-protein kinases Erb-B2, 3, and/or 4 (ERBB2, ERBB3, ERBB4), CD19, CD20, CD5, CD7, CD10, CD22, CD30, CD33 (CD33/IL3Ra), CD34, CD38, CD41, CD44, CD49f, CD56, CD74, CD123, CD133, CD138, CD171, antigen of a cytomegalovirus (CMV) infected cell (e.g., a cell surface antigen), epithelial glycoprotein2 (EGP2), epithelial glycoprotein-40 (EGP-40), epithelial cell adhesion molecule (EpCAM), folate-binding protein (FBP), fetal acetylcholine receptor (AChR), folate receptor-α, Ganglioside G2 (GD2), Ganglioside G3 (GD3), human telomerase reverse transcriptase (hTERT), interleukin-13 receptor subunit alpha-2 (IL-13R-α2), kappa-light chain, kinase insert domain receptor (KDR), Lewis A (CA19.9), Lewis Y (LeY), L1 cell adhesion molecule (L1CAM), melanoma antigen family A1 (MAGE-AI), MAGEA3, Mucin 16 (Muc-16), Mucin 1 (Muc-1), Mesothelin (MSLN), NKG2D ligands, cancer-testis antigen NY-ESO-1, oncofetal antigens (e.g., h5T4), prostate stem cell antigen (PSCA), prostate-specific membrane antigen (PSMA), tumor-associated glycoprotein 72 (TAG-72), vascular endothelial growth factor R2 (VEGF-R2), and Wilms tumor protein (WT-1), ROR1, c-Met, Glycolipid F77, EGFRvIII, TCR; carbonic anhydrase IX (CAIX), carcinoembryonic antigen (CEA), tumor associated glycoprotein 72 (TAG72); GP100; MART1; p53; BCMA or CS-1.

In some embodiments, the activator cells described herein may be engineered to express a cell-surface antigen such as CD19, Her2/Erbb3, or EGFR. In some embodiments, the activator cells are engineered to express a variant form of an endogenous antigen, such as a truncated variant of human CD19 (tCD19) which lacks signaling function. In some embodiments, the activator cells are engineered to express a cell-surface antigen by lentiviral transduction prior to co-culture with the RE-cells.

In some embodiments, the activator cells may be further engineered to express an immunosuppressive molecule known to modulate (e.g., suppress) the activity of an effector cell in a tumor microenvironment, such as an immune checkpoint protein. In such embodiments, the expression of the immunosuppressive factor by the activator cell allows for identification of genes that modulate (e.g., increase or decrease) the signaling events associated with expression of that particular protein. For example, in some embodiments, the activator cells described herein may be engineered to express an immune checkpoint protein, such as PDL-1, BTN3a1a, BTNL2, C10of54 (VISTA), B7-H3 (CD276), and/or B7-H4 (VTCN1).

CRISPR/Cas9 and Screens

In some embodiments, the RE-cells or the activator cells described herein are further engineered to express a Cas9 protein and a guide RNA (gRNA) library. Genome-wide and subgenome-scale screens using CRISPR/Cas9 systems have been performed when screening for essential genes in a cancer cell autonomous setting (Wang et al. 2015 Science 350:1096; Wang et al. 2014 Science 343:80; Gilbert et al. 2014 Cell 159:647) or when screening for resistance genes towards infectious agents, such as West Nile Virus (Ma et al. 2015 Cell Reports 12:673; Zhang et al. 2016 535:164).

In some embodiments, the present invention provides methods of engineering RE-cells to express a Cas9 protein. Cas9 protein can be derived from *Streptococcus pyogenes* (spCas9) or other bacteria strains including *Staphylococcus aureus* (saCas9). In addition, CRISPR/Cas9 screens can be performed using the CRISPRi systems (Gilbert et al. 2014 Cell 159:647) in which the Cas9 protein is engineered to be catalytically inactive (dCas9) and is fused to the transcriptional repressor KRAB. Instead of loss-of-function screens driven by DNA cutting, CRISPRi represses the transcription of genes. In addition, CRISPRa screens can be performed wherein genes are activated rather than suppressed using dCas9-Sun together with single chain-VP64 fusion proteins (Gilbert et al. 2014 Cell 159:647).

In some embodiments, the present invention provides methods of engineering RE-cells to express a guide RNA (gRNA) library. As used herein, a "guide RNA" or "gRNA" refers to a short RNA molecule capable of directing a Cas9 endonuclease to a specific target genomic sequence. In general, an active gRNA comprises a nucleotide sequence that recognizes a targeted genomic region of the host DNA (i.e., a crRNA) and a tracrRNA sequence capable of binding Cas9. Association of a crRNA and a tracrRNA forms an active gRNA complex capable of binding to both the target DNA sequence and a Cas9 protein. In some embodiments, the crRNA and tracrRNA are comprised in two separate RNA molecules, which associate to form a functional gRNA complex. In certain embodiments, the crRNA and tracrRNA are comprised in a single RNA sequence, known as a single guide RNA (sgRNA). In certain embodiments, the crRNA portion of the sgRNA and the tracrRNA portion of the sgRNA form a hairpin structure.

As used herein "genome-wide gRNA library" means a gRNA library constructed to target genomic elements across substantially all of the genome. Similarly, as used herein the term "subgenome-scale gRNA library" means a gRNA library constructed to target a portion of the genome (i.e. less than the entire genome). In general, a gRNA library (either genome-wide or subgenome-scale) will comprise multiple gRNAs that target the same genetic locus. For example, a gRNA library may comprise 2, 3, 4, 5, 6, 7, 8, 9, 10, 11, 12, 13, 14, 15, or more gRNAs per gene. In general, genome wide gRNA libraries can be utilized for in vitro screens. For in vivo screens, it is contemplated that ideally, sub-genome scale screens will be used. For example, a subgenome-scale gRNA library may comprise gRNAs targeting approximately 2000, 3000, 4000, 5000, 6000, or more genes with 3-10 guides per gene. However, the subgenome-scale screen may be varied. For example, in certain embodiments, specialized gRNA libraries targeting surface receptors, T cell associated genes, immune related genes, and/or specific signaling pathways may be used.

In some embodiments of the present invention, the nucleic acid encoding the Cas9 protein, the antibiotic resistance cassette, and the gRNA guide library may be introduced by lentiviral transduction. As described herein, successful transduction of Cas9-encoding lentivirus into polyclonal populations of primary T cells was not possible with standard titers of lentivirus (e.g., $10 \times 10^5$ infectious units/mL). However, the present inventors have unexpectedly found that high titers of Cas9-encoding lentivirus result in successful transduction of polyclonal populations of primary T cells. Herein, a "high-titer" of Cas9-encoding lentivirus refers to viral titers greater than standard titers of lentivirus commonly used in the art. In some embodiments, a high titer of Cas-9 encoding lentivirus is a lentiviral titer of greater than $10 \times 10^5$ infectious units/mL, greater than $10 \times 10^6$ infectious units/mL, or greater than $10 \times 10^7$ infectious units/mL. In some embodiments, the Cas9-encoding lentiviral vector is introduced to primary cells or cell lines at a titer of at least $10 \times 10^6$ infectious units/mL. In some embodiments, the Cas9-encoding lentiviral vector is introduced to primary cells or cell lines at a titer of at least $10 \times 10^7$ infectious units/mL. Titers of Cas9 lentivirus of at least $10 \times 10^6$, preferably of at least $10 \times 10^7$ infectious units/mL can be achieved using techniques known in the art for purification and concentration of lentivirus. (See for example, Jiang et al. 2015 Sci. Rep. 5:13875; Cooper et al. 2011 J. Virol. Methods 177:1-9; Tiscornia et al. 2006 Nature Protocols 1:241-245; Geraerts et al. 2005 J. Gene Med. 7:12991310).

In some embodiments, a primary cell or cell line is engineered to express Cas9 by electroporation of a nucleic acid encoding the Cas9 protein. In some embodiments, a primary cell or cell line is engineered to express Cas9 by electroporation of an mRNA transcript encoding the Cas9 protein. In such embodiments, the Cas9 protein is transiently produced in the cell. In some embodiments, the primary cell or cell line is engineered to express a gRNA library and an antibiotic resistance cassette by lentiviral transduction and further engineered to express Cas9 by electroporation of an mRNA transcript encoding the Cas9 protein. In general, the introduction of the gRNA library and antibiotic resistance cassette and the introduction of the nucleic acid encoding Cas9 to the primary cell or cell line may occur in any order (i.e., the gRNA/antibiotic resistance cassette may be introduced first and the Cas9-encoding nucleic acid second, or the Cas9-encoding nucleic acid may be introduced first and the gRNA/antibiotic resistance cassette second). However, in preferred embodiments, the gRNA library is introduced first, followed by electroporation with mRNA transcripts encoding a Cas9 protein. Performing the steps in this order allows for increasing the number of viable engineered cells to be used in the screening methods described herein.

The general experimental schematic of a CRISPR/Cas9 screen is the introduction (e.g., by lentiviral transduction) of an antibiotic resistance cassette together with a library of guide RNAs (gRNAs) targeting either the whole genome or a sub-genome of genes to a primary cell or cell line that has been engineered to express Cas9 in vitro. Successfully transduced cells are identified by antibiotic selection, and comprise at least one edited gene loci. In some embodiments, the primary cell or cell line containing the Cas9 and gRNAs are subjected to an environmental stimulus in order to assess genes and/or pathways that modulate a cellular response to the environmental stimulus. In some embodiments, the primary cell or cell line containing the Cas9 and gRNAs are cultured for a period of time to assess genes required for survival. In some embodiments, the primary cell or cell line containing the Cas9 and gRNAs are cultured for at least 7 days. In some embodiments, the RE-cells and activator cells are co-cultured for at least 7 days.

In some embodiments, the RE-cells and activator cells are cultured for a period of time to assess the effect of a particular gene(s) on survival and/or cell death of the RE-cells and/or the activator cells. Cell survival and/or cell death of an engineered cell and/or a target cell may be assessed in a variety of ways known in the art, including counting viable cells using a hemocytometer, flow cytometry to measure expression of apoptotic cell surface markers (e.g., Annexin V or phosphotidylserine) or markers of cellular necrosis (e.g., propidium iodide), and/or release of intracellular molecules such as intracellular proteases.

Figure 2:
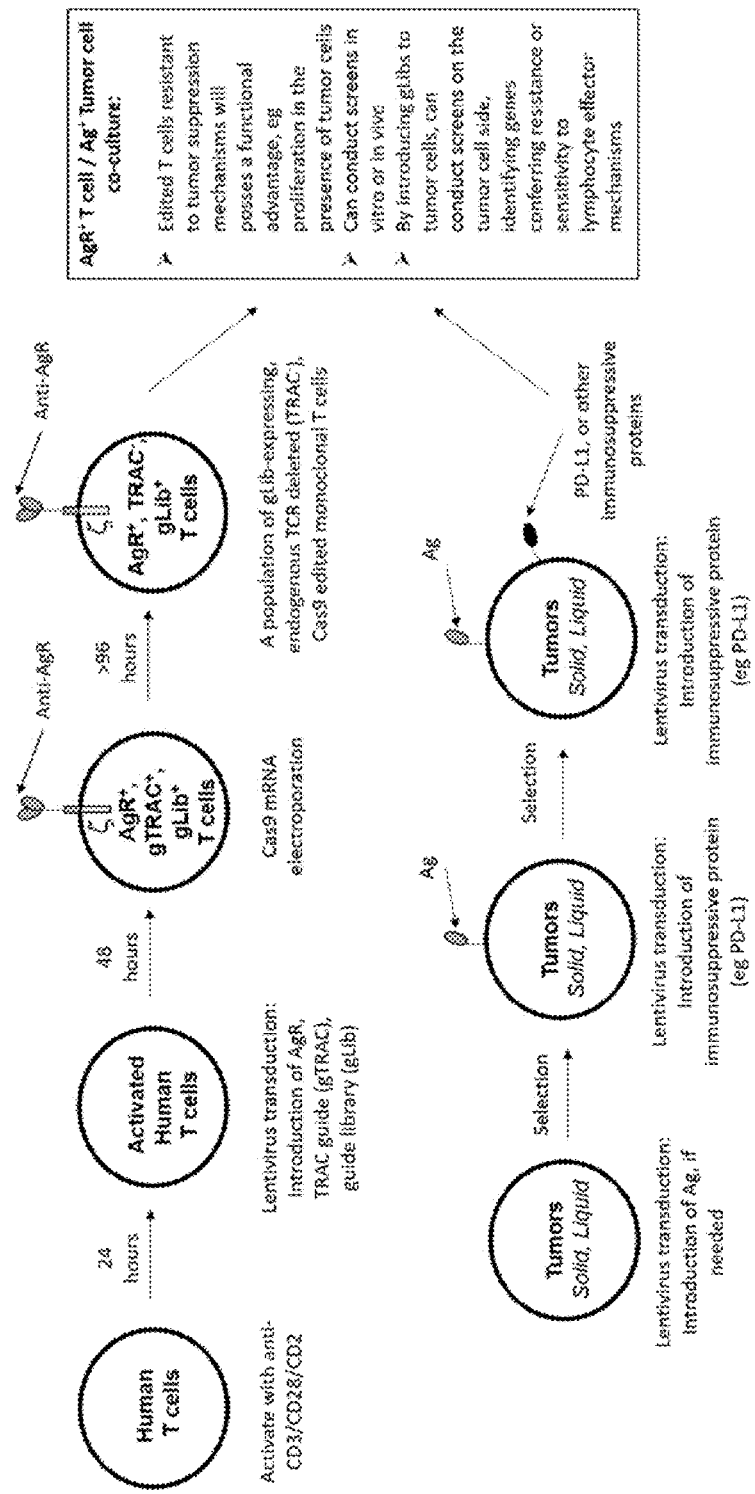
FIG. 2 illustrates a work-flow for producing a population of $CAR^+$, $TRAC^-$, $gLib^+$, Cas9-edited T cells for screening for genes controlling the ability of T cells to generate an anti-tumor response and tumor cells engineered to express an antigen (Ag) recognized by the engineered T cells.

In some embodiments, CAR-T cells comprising a CAR specific for a target protein on an activator cell, a Cas9 protein, and a gRNA library are co-cultured with activator cells expressing the target protein. In some embodiments, the activator cell are further engineered to express an immunosuppressive molecule. A general workflow for RE-cell and activator cell engineering and co-cultures is shown in FIG. 2. As shown in FIG. 2, a human T cell is activated through triggering of the T cell receptor complex and CD28, and 24 hours later transduced with a lentivirus expressing a chimeric antigen receptor (CAR), a guide targeting the TRAC gene (gTRAC), and a guide targeting a gene of interest as part of a guide library (gLib). Following transduction, the CAR-expressing T cell is engineered to express a Cas9 protein by electroporation of Cas9 mRNA. After further in vitro expansion, edited T cells are selected by enriching for T cells lacking CD3 expression, which is lost upon successful editing of the TRAC gene. A population of CAR+, TRAC−, gLib+, Cas9-edited T cells are subsequently obtained for screening for genes controlling the ability of T cells to generate an anti-tumor response. Herein, an "anti-tumor response" refers to the ability of an immune cell (e.g., an RE-cell) to recognize and destroy, kill, or otherwise control a tumor cell. In such embodiments, an anti-tumor response may be measured by the cytotoxic effects of the RE-cell against a tumor cell, for example by direct cytolysis, increased production of pro-inflammatory cytokines by the engineered immune cell (e.g., IFNγ, IFNα, TNFα, IL-6, IL-8, I-1β, IL-12, etc.).

In some embodiments, the Cas9-edited RE-cells (e.g., Cas9-edited T cells) that are resistant to tumor suppression mechanisms will demonstrate a functional advantage over Cas9-edited RE-cells that are not resistant to tumor suppression mechanisms. For example, in some embodiments, the Cas9-edited RE-cells that are resistant to tumor suppression mechanisms will demonstrate increased proliferation and/or prolonged survival in culture. In some embodiments, the Cas9-edited RE-cells and the activator cells are co-cultured for at least 7 days. In some embodiments, the Cas9-edited RE-cells and the activator cells are co-cultured for at least 10, at least 15, at least, 20, or at least 30 days.

In particular embodiments, the methods described herein allow for the identification of genes that mediate or are associated with resistance to tumor suppression mechanisms. Such genes can be identified by sequencing of gRNA sequences extracted from engineered cells. In such embodiments, total DNA is extracted from engineered cells and gRNA sequences are amplified by polymerase chain reaction (PCR) to generate a plurality of gRNA amplicons. Sequencing of the gRNA amplicons allows for the identification of gRNA sequences that present in the population of engineered cells obtained at the conclusion of the assay. In particular embodiments, the sequencing comprises high-throughput sequencing. In particular embodiments, the sequencing comprises next-generation sequencing techniques. The identity of individual gRNA sequences present at the end of the assay may be mapped to the corresponding target gene. In some embodiments, one or more gRNA sequences are enriched in or depleted from the population of Cas9-edited RE-cells that are resistant to tumor suppression as compared to controls. For example, if a particular gRNA sequence, or group of gRNA sequences, is enriched or increased in the resistant Cas9-edited RE-cells at the end of the assay compared to controls, the gene targeted by that particular gRNA or group of gRNAs may target genes that negatively regulate effector cell activation, proliferation, and/or survival as inactivation of that particular gene or group of genes (e.g., by the introduction of double-stranded DNA breaks) resulted in an increase in the number or percentage of cells comprising that particular gRNA or group of gRNAs, potentially through increased cell survival or increased cell proliferation.

Conversely, if a particular gRNA sequence, or group of gRNA sequences, is depleted or decreased in the resistant Cas9-edited RE-cells at the end of the assay compared to controls, the gene targeted by that particular gRNA or group of gRNAs may target genes that positively regulate effector cell activation, proliferation, and/or survival as inactivation of that particular gene or group of genes (e.g., by the introduction of double-stranded DNA breaks) resulted in a decrease in the number or percentage of cells comprising that particular gRNA or group of gRNAs, potentially through decreased cell survival or decreased cell proliferation.

All patent applications and publications, scientific publications, and web-sites mentioned in this document are hereby incorporated by reference herein for the teachings for which they are cited, as if fully set forth in this specification.

The invention described and claimed herein is not to be limited in scope by the specific aspects or embodiments herein disclosed, since these aspects are intended as illustrations of several aspects of the invention. Any equivalent aspects and embodiments are intended to be within the scope of this invention. Indeed, various modifications of the invention in addition to those shown and described herein will become apparent to those skilled in the art from the foregoing description. Such modifications are also intended to fall within the scope of the appended claims.

EXAMPLES

Example 1: Generation of CAR-Expressing, Guide-Library Containing, Cas9-Edited T Cells Creating Chimeric Antigen Receptors CARs specific for human CD19, Her2/Erbb2, and EGFR proteins were generated. Briefly, the 22 amino acid signal peptide of the human granulocyte-macrophage colony stimulating factor receptor subunit alpha (GMSCF-Rα) was fused to an antigen specific scFv domain, with the human CD8a stalk serving as a transmembrane domain. The signaling domain of CD3ξ was then fused to the cytoplasmic end of the CD8α stalk. For anti-CD19 CARs, the scFv was derived from the anti-human CD19 clone FMC63. To create a CAR specific for human HER2/ERBB2, the anti-human HER2 scFv derived from trastuzumab was used. Similarly, to generate a CAR specific for EGFR, the anti-EGFR scFv derived from cetuximab was used.

Generation of CAR- and Guide RNA-Expressing Lentivirus

To generate lentiviruses containing a CAR expression cassette together with a library of guides, 289×10$^6$ of LentiX-293T cells were plated out in a 5-layer CellSTACK 24 hours prior to transfection. Serum-free OptiMEM and TransIT-293 were combined and incubated for 5 minutes before combining helper plasmids (58 μg VSVG and 115 μg PAX2-Gag-Pol) with 231 μg of a plasmid comprising, in order: a mouse U6 promoter expressing a guide library; a human U6 promoter expressing a guide targeting the TRAC gene; and a SFFV promoter driving expression of a CAR cassette followed by a T2A sequence and a puromycin resistance cassette. After 20 minutes, this mixture was added to cells with fresh media. Media was replaced 18 hours after transfection and viral supernatants were collected 48 hours post-transfection. Supernatants were treated with Benzonase® nuclease and passed through a 0.45 μm filter to isolate the viral particles. Virus particles were then concentrated by Tangential Flow Filtration (TFF), aliquoted, tittered, and stored at −80° C.

CD8 T Cell Isolation and Activation

Total human PBMCs were isolated from fresh leukopacks by Ficoll gradient centrifugation. CD8+ T-cells were then purified from total PBMCs using a CD8+ T-cell isolation kit (Stemcell Technologies Cat #17953). For T cell activation, CD8+ T cells were plated at 2×10⁶ cells/mL in ImmunoCult-XF T Cell Expansion Medium (StemCell Tech #10981) in a T75 flask (15 mL volume), with 25 μL/mL of ImmunoCult T-cell activators (anti-CD3/CD28/CD2, StemCell Technologies, Vancouver BC, Canada) and 10 ng/mL human IL2. T-cells were activated for 18 hours prior to transduction with lentiviral constructs.

Lentiviral Transduction of T Cells

CD8+ T-cells activated 18 hours prior were seeded at 3×10⁶ cells per well in a 6-well plate, in 1.9 mL volume of Immunocult-XF Media, 10 ng/mL human IL2 and Immunocult T-cell activators (Day 1). Lentivirus was added at an MOI capable of infecting 80% of all cells. Retronectin (20×) was added to each well for a final concentration of 1×. Plates were spun at 600×g for 1.5 hours at room temperature. After 18 hours (Day 2), cells were washed and seeded at 1×10⁶ cells/mL in Immunoult-XF, 10 ng/mL IL2+ T-cell activators. The lentiviral constructs used to generate CAR-T responder cells contained the EF1α promoter expressing the CAR together with a murine U6 promoter driving expression of a guide targeting the TRAC gene, which encodes the a chain of the T cell receptor (TCR), and the B2M gene, which encodes beta-2 microglobulin. The constructs further contained a human U6 promoter driving expression of a guide library to be used for CRISPR/Cas9 screening purposes.

Cas9 mRNA Transfection of T Cells

On Day 3, Cas9 mRNA was electroporated into T cells. Briefly, activated T cells transduced with the CAR and guide RNA expressing lentiviral constructs T cells were harvested and suspended in nucleofection buffer (18% supplement 1, 82% P3 buffer from the Amaxa P3 primary cell 4D-Nucleofector X kit S (Cat #V4XP-3032)) at a concentration of 100×10⁶ cells/mL. 4 μg (4 μL) of cytosine methylated *Streptococcus pyogenes* Cas9-NLS mRNA (Trilink L-6125) was added per 20 μL of cell solution, and 24 μL of cell/mRNA mixture was added to each electroporation reaction well according to the manufacturer's recommendations. Cells were electroporated according to the "Nucleofection of activated CD8 T-cells" program (EO-115). After electroporation, 80 μL of warm Immunocult-XF media was added to each well and cells were removed and pooled into a culture flask at a density of 2×10⁶ cells/mL in Immunocult-XF media containing IL-2 (10 ng/mL). On Days 4-8, cells are washed, counted, and seeded at densities of 1×10⁶ cells/mL in Immunocult-XF media+10 ng/mL IL-2 to allow for Cas9 editing of the TRAC and B2M genes.

Example 2: Characterization of Engineered T Cells

Figure 3A:
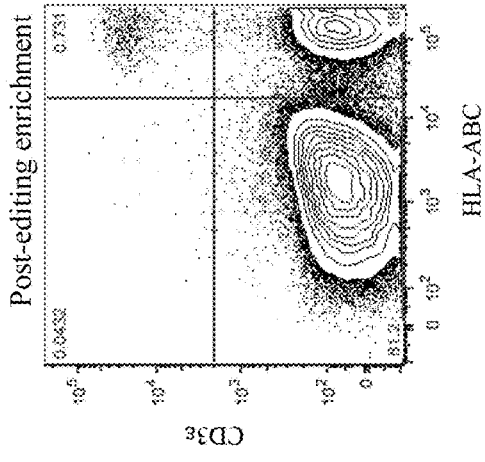
FIG. 3A-FIG. 3D depicts CD3 and HLA expression on T cells before and after engineering into edited CAR-T cells.
Figure 3B:
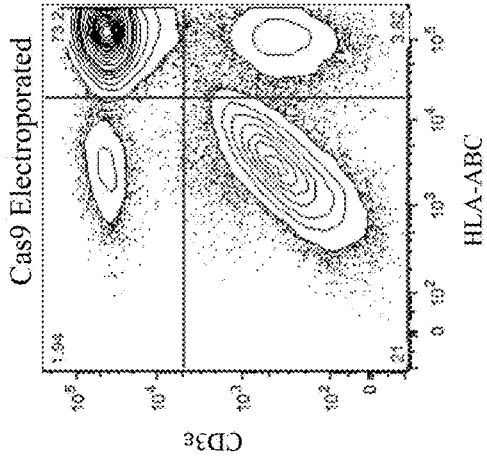

Prior to engineering, the isolated primary human T cells expressed CD3 as part of the endogenous TCR complex (FIG. 3A). In general, T cells are transduced with a CAR-expression construct also comprising a guide RNA targeting the TRAC gene and a library of guide RNAs. In this example, T cells were transduced with a lentivirus expressing a CAR, a guide RNA targeting the TRAC gene, and a guide RNA targeting the B2M gene used to assess the editing of non-TCR genes as a proxy for gene editing by the guide RNA library. Following lentiviral transduction and editing by Cas9 mRNA electroporation, successfully transduced and edited T cells demonstrate a loss of CD3 expression due to editing of the TRAC gene, which encodes a critical component of the TCR complex (FIG. 3B). Genes targeted by library guides will also undergo editing events, as illustrated by loss of HLA-ABC expression due to the expression of the B2M guide RNA (FIG. 3B).

Figure 3C:
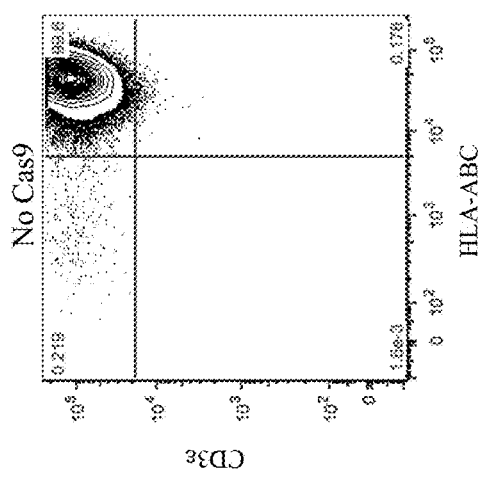
Figure 3D:
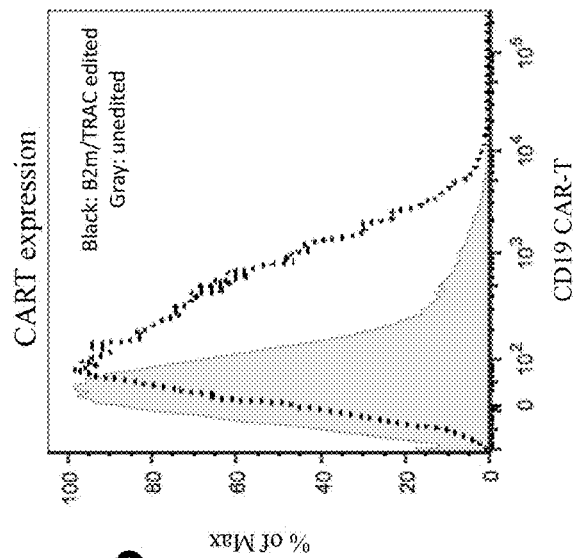

Successfully edited and engineered T cells were consequently identified by loss of CD3 expression, with edited T cells enriched by removal of CD3-expressing T cells by magnetic beads. Briefly, on Day 10 after Cas9 transfection, cells were removed from the culture flasks, and unedited CD3-expressing cells were removed from the bulk population by two rounds of CD3 magnetic selection using the EasySep human CD3 positive selection kit (StemCell Tech Cat #18051) to produce an enriched population of Cas9-edited, CD3-negative T cells (FIG. 3C), and CD19 CAR expression on the edited, CD3-negative cells was determined using a CD19/fluorescently labelled tetramer. The edited CD3-negative cells demonstrate expression of the CD19 CAR in comparison to non-engineered T cells (FIG. 3D). The resultant pure population of CAR-expressing, guide library containing, Cas9-edited T cells was were then frozen in CS-10 media for further experimentation. In this particular example, we have included a guide that targets the B2M gene in place of a guide library.

Example 3: Engineering of Solid and Liquid Tumors to Express Antigens and Inhibitory Molecules Two cell lines, non-adherent Raji-Luciferase (Raji) cells (Genscript Sample ID C01X01) and adherent DLD-1 cells (ATCC #CCL-221) were acquired and engineered to express various cell-surface antigens and inhibitory molecules. Both Raji and DLD-1 cells were routinely cultured in RPMI-1840 media containing 10% FBS and 1× penn/strep. Plasmids for various inhibitory molecules containing blasticidin resistance cassettes were designed and synthesized by Genscript. Expression vectors for PDL-1, BTN3a1a, BTNL2, C10of54 (VISTA), B7-H3 (CD276), B7-H4 (VTCN1), and IDO correspond to the following KSQ nomenclature pKSQ022, pKSQ033, pKSQ034, pKSQ035, pKSQ036, pKSQ037, and Nick_pKSQ037, respectively. The expression vector for CD19 was also synthesized by Genscript and corresponds to pKSQ019 according to KSQ nomenclature.

For each cell line to be engineered, 2×10' cells in 500 μL were seeded in one well of a 6-well tissue culture plate on Day 0. On Day 1, 500 μL of virus and polybrene at a final concentration of 8 μg/mL were added to each well. A control well containing 2×10⁵ cells and polybrene without virus was added to each plate to assess antibiotic killing/resistance. After addition of virus, the plates were spun down at 600×g for 90 minutes and incubated at 37° C. for 18 hours. After the incubation, the cells were spun down at 300×g, the media was removed and replaced with media containing 10 μg/mL blasticidin (for Raji cells) or 20 μg/mL blasticidin (for DLD-1 cells). When complete killing of control wells containing un-transduced parental cells and blasticidin was observed (~5 days), the transduced cells were expanded.

Raji cells were transduced with expression vectors for PDL-1 (pKSQ022), BTN3a1a (pKSQ033), BTNL2 (pKSQ034), VISTA (pKSQ035), CD276 (pKSQ036), VTCN1 (pKSQ037), or IDO (Nick_pKSQ037) as described above. Cells were then sorted based on expression levels of each transduced protein using the following PE anti-human antibodies: PDL-1 (BD #561787), BTN3a1a (Sony #2313520), VISTA (RnD Systems #FAB71261P), CD276 (Sony #2355020), and VTCN1 (Biolegend #358104) on a Sony LE-SH800ZFP sorter. Sorted cells expressing high levels of the transduced proteins were then expanded in the presence of 10 µg/mL blasticidin and frozen down as polyclonal populations. Raji cells expressing BTNL2 and those expressing IDO were not sorted prior to freezing down polyclonal populations. To generate monoclonal cell lines, polyclonal lines were again sorted for high expression of each protein, excluding the IDO-expressing Raji cell line. Cells expressing high levels of transduced protein were collected and then serial diluted in a 96 well plate by adding 10,000 cells to well A1 in 200 µL media not containing blasticidin. 100 µL from well A1 was serial diluted 1:2 down through well H1. 100 µL of media was then added to each well in column 1 (A1-H1) and then serial diluted across 1:2 resulting in several wells containing only 1 cell. Cells were incubated at 37° C. and observed for single cell colony expansion in the absence of antibiotic selection. Following monoclonal expansion, cells were stained for their respective proteins to confirm expression and were then frozen down.

DLD-1 cells were transduced with the expression vector for CD19 as described above. CD19 expression was analyzed by staining the transduced cells with a PerCp-labeled anti-human CD19 antibody (Biolegend #363016). The resultant cells were then frozen down as a polyclonal population. DLD-1 expressing CD19 were then further engineered to express various inhibitory proteins including PDL-1, BTN3a1a, BTNL2, VISTA, CD276, and VTCN1, as described above. DLD-1 cells expressing both CD19 and inhibitory protein DLD-1 cell lines were FACS sorted for high expression and polyclonal lines were frozen down. Monoclonal cell lines were generated by single-cell cloning. The expression of CD19 and inhibitory proteins on the monoclonal cell lines was determined by flow cytometry (FIG. 4B) and the cells were then subsequently frozen down.

Figure 4A:
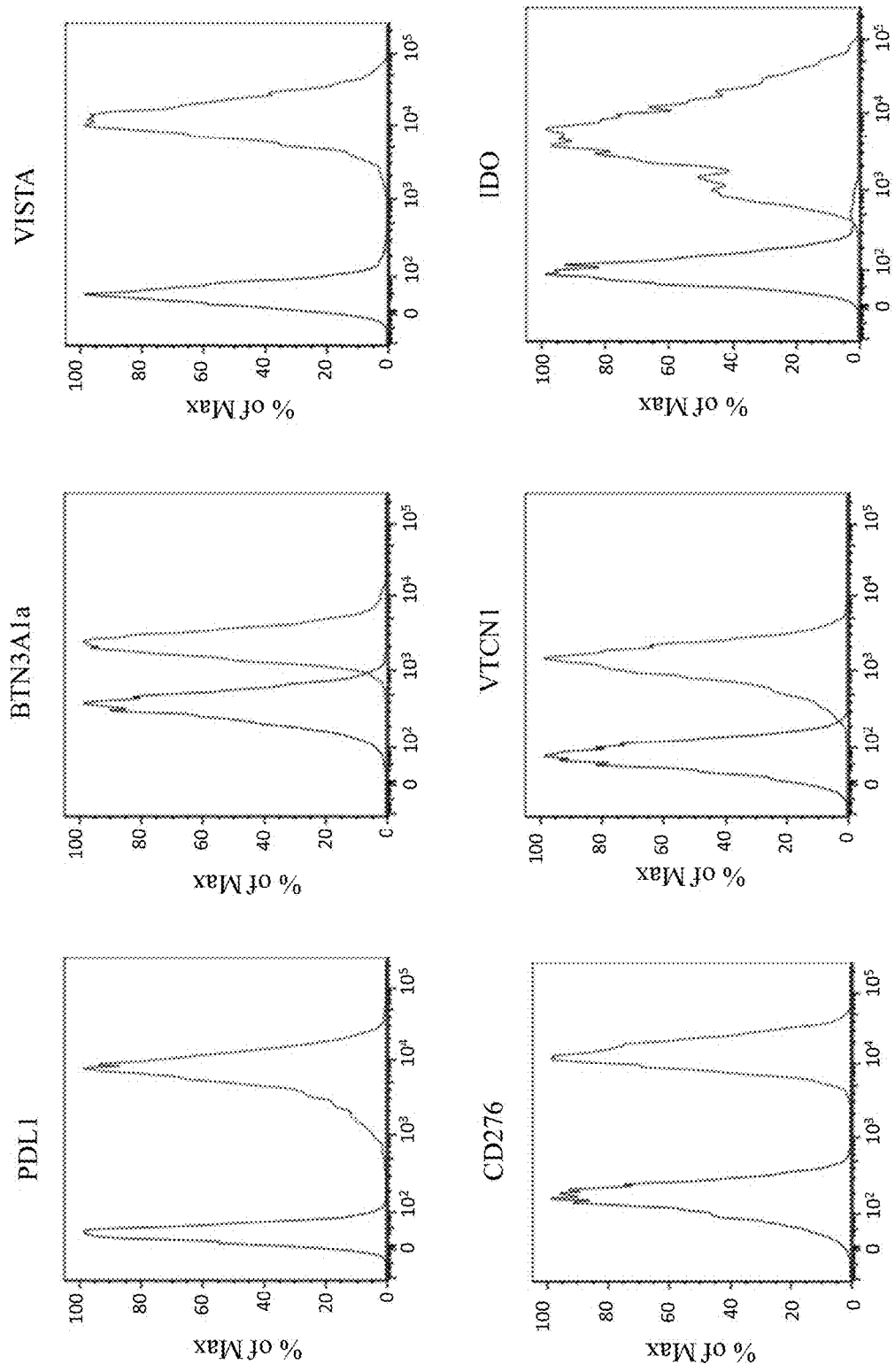
FIG. 4A-FIG. 4B show Raji cells engineered to express a number of immunosuppressive molecules, such as PD-L1, BTN3A1a, VISTA, CD276, VTCN1 and IDO.
Figure 4B:
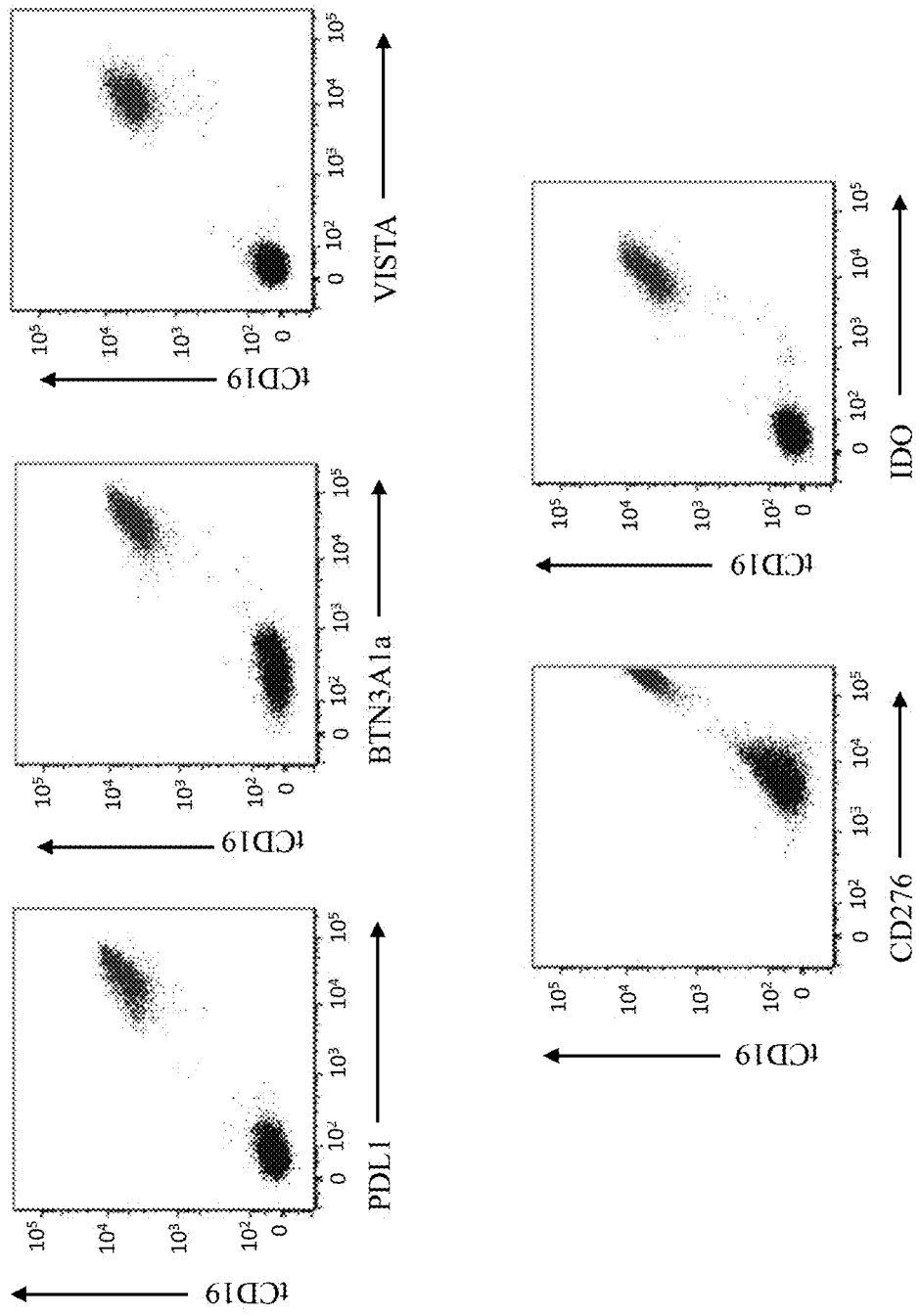

As shown in FIG. 4A, Raji cells transduced with expression constructs for inhibitory molecules demonstrated enhanced inhibitory molecule expression compared to non-transduced parental cells (FIG. 4A, with parental cells as the left peak and engineered cells as the right peak). FIG. 4B shows DLD1 cells engineered to express a truncated version of CD19 lacking cytoplasmic signaling functionality (tCD19, y-axis)) and immunosuppressive molecules, including PD-L1, BTN3A1a, VISTA, CD276, and VTCN1 (X-axis). Cells in the upper-right hand corner of the FACS plot represent engineered DLD1 cells, and cells in the lower left hand corner represent parental DLD1 cells.

Example 4: Functional Validation of Edited T Cells Expressing CARs Specific for HER2

Her2-CAR containing lentiviruses were generated as described in Example 1. To assess the function of the Her2-CAR constructs, recombinant Erb2/Her2-Fc protein (R&D systems cat1129-ER-050) was dissolved in PBS and a log 2 dilution series was made, with final concentrations ranging from 0.8 µg/mL-100 µg/mL. Recombinant protein was coated onto the wells of a 96-well tissue culture treated flat bottom plate by incubating 100 µL of Her2-protein solution at 37° C. for 2 hours. Activation was assessed by culture of CAR-expressing Jurkat T cells on plate-bound Her2 protein. Briefly, 100,000 Her2-CAR expressing Jurkat cells were cultured on top of recombinant Erb2/Her2-Fc protein coated wells in RPMI supplemented with 10% FBS for 4 hours. Cells were then stained on ice with antibodies against CD69 (clone FN50, BV786 conjugated, BD biosciences) and CD69 expression was assessed by flow cytometry on a BD Fortessa X-20.

Figure 5:
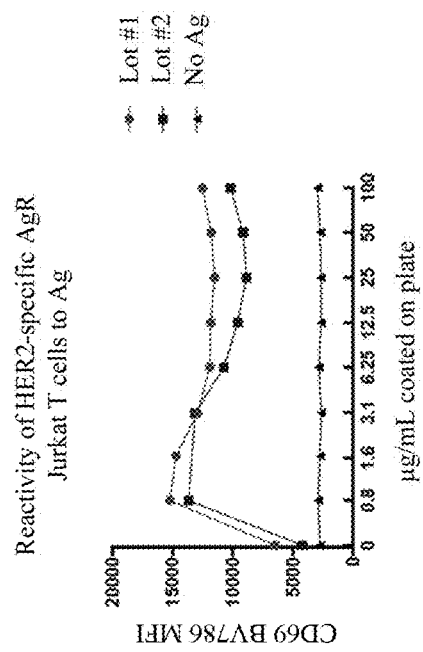
FIG. 5 shows Jurkat T cells engineered to express CARs specific for Her2 recognizing and becoming activated in response to immobilized, recombinant Her2.

These results demonstrate that Jurkat cells expressing either of the Her2 CAR constructs were reactive to the recombinant Her2 protein, as demonstrated by an increase in CD69 expression on the Jurkat cells after 4 hours of culture (FIG. 5).

Figure 6A:
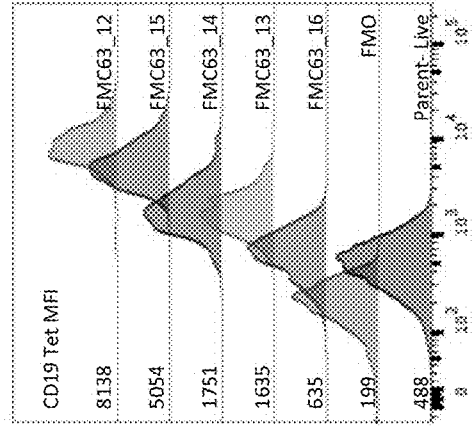
FIG. 6A-FIG. 6C shows T cells engineered to express CARs recognizing the CD19 antigen at varying affinities.
Figure 6B:
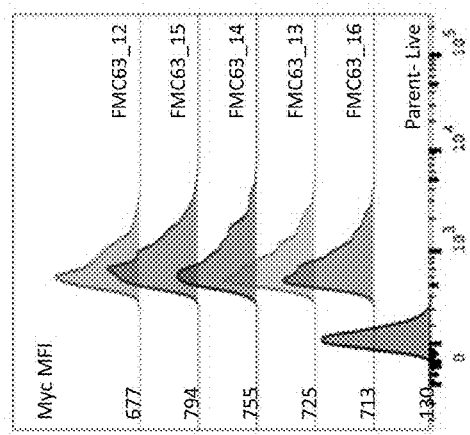

Example 5: Functional Validation of T Cells Expressing De-Affinity Matured CD19 CARs The affinity of a TCR for MHC usually falls within the range of 1-100 M, and the published affinity of FMC63 falls within the low nM range. Therefore, CD19 CAR constructs were generated to reduce the affinity of FMC63 for CD19 to a more physiologically relevant range. The FMC63_12 construct (FIG. 6) is the parental clone, and FMC63_13, 14, 15 and 16 all contain mutations designed to reduce relative affinity to CD19. FMC63_13, 14, 15 and 16 are referred to as "de-affinity CARs." Jurkat cells expression FMC63 parental and de-affinity CARs comprising a Myc tag were generated by lentiviral transduction as described in Example 1. CAR expression assessed by FACS using a fluorescently labelled anti-Myc antibody. As shown in FIG. 6A, transduced Jurkat cells expressed the parental and de-affinity CARs at similar levels. In FIG. 6B, the transduced Jurkat cells were assessed for relative binding affinity to the CD19 target antigen using fluorescently labelled CD19 tetramers.

Figure 6C:
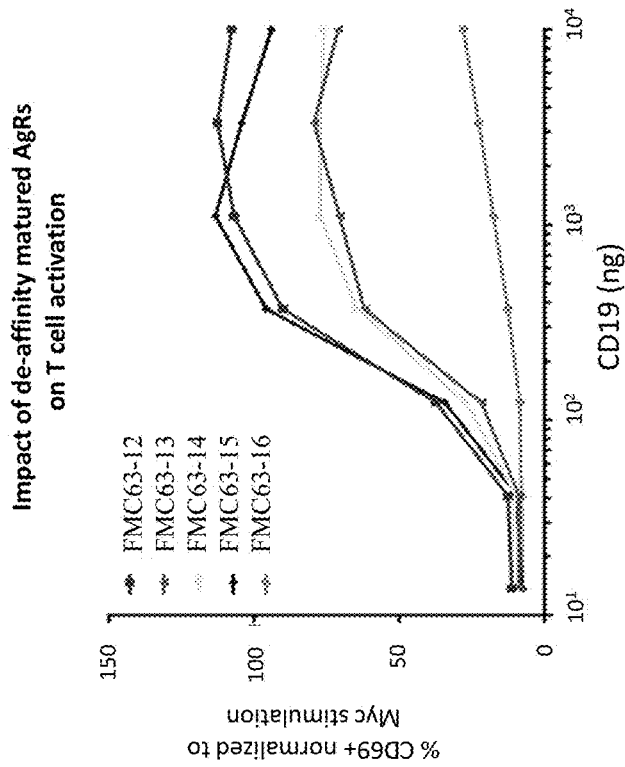

Activation and function of FMC63 de-affinity CARs was assessed by culture of CAR-expressing Jurkat T cells on plate-bound CD19 protein, and examination of CD69 induction by FACS. Briefly, a 100 µL of log 3 dilution series (ranging from 0.14 µg-100 µg/mL) of recombinant CD19 Fc chimera protein was coated onto the wells of a high-binding 96 well plate (Corning) overnight at 4° C. The plates were washed with PBS, and 100,000 Jurkat E6-1 cells expressing CARs FMC63_12, FMC63_13, FMC63_14, FMC63_14, FMC63_15, or FMC63_16 were seeded in the wells in 200 µL of RPMI supplemented with 10% FBS for 4.5 hours at 37° C. Cells were harvested, Fc receptors were blocked using Human TruStain FcX™ (Biolegend), and stained with anti-human CD69 (clone FN50, BD Biosciences) and anti-Myc antibody (Thermofisher, Cat #R95325) for 30 min at 4° C. Cells were run on BD Fortessa and data were analyzed using Flow Jo. As shown in FIG. 6C, the engineered Jurkat T cells recognize and are activated in response to immobilized, recombinant CD19. The affinity of different FMC63 derivatives was observed to rank FMC63_12>FMC63_15>FMC63_14>FMC63_13>FMC63_16.

Example 6: An In Vitro Screen Demonstrating the Identification of PD1 as the Regulator of PD-L-Mediated Immunosuppression CAR-expressing, guide-library containing, Cas9-edited T cells (CARTs) were generated as stated in Example 1. 20×10$^6$ CARTs were seeded at 1×10$^6$ cells/mL in Immunocult-XF media containing IL-2 (10 ng/mL) for each screen. Parental Raji cells and Raji cells engineered to express transgenic human PD-L1 (generated as stated in Example 3) were treated with mitomycin (Sigma #M4287-2MG) prior to the commencement of the screen. Briefly, a 500 µg/mL solution of mitomycin was prepared by adding 4 mL of distilled water to the stock vial. Mitomycin was further diluted in PBS to a final concentration of 50 µg/mL. Raji cells were re-suspended to no greater than 50×10$^6$ cells/mL in PBS containing mitomycin at a concentration of 50 µg/mL and incubated at 37° C. for 20 minutes in the dark. Raji cells were then washed in 40× the volume of PBS (300 g for 5 minutes) two times to remove residual traces of mitomycin. On Day 1, CARTs and parental Raji or Raji expressing PD-L1 were co-cultured at an effector to target ratio (E:T) of 3:1 (e.g. 20×10$^6$ CARTs with 6.6×10$^6$ Raji cells). In order to maintain a 3:1 E:T ratio, tumor cells were routinely added to the screens when complete Raji cell clearance was observed (every 2-3 days). To quantify and monitor the E:T ratio, a 250 µL aliquot was removed from the culture every 2 days. Cells were spun down at 300×g for 5 minutes and re-suspended in flow cytometry staining buffer (FACS buffer) (Biolegend #420201). Trustain Fc block (Biolegend #422302) was added as per manufacturer's instructions for 5 minutes prior to the addition of staining antibodies. An antibody cocktail containing one test of anti-human CD8 BUV395 (BD Bioscience #563795) and CD19 PerCp (Biolegend #363016) was prepared and used for the entire screen. One test of the antibody cocktail was added to each sample followed by the addition of an e780 Live/Dead solution (Ebioscience #65-0865-14) diluted 1:500. Samples were stained for 20 minutes at 4° C. in the dark and then washed twice. Each sample was then re-suspended in 100 µL FACS buffer containing 2×10$^{-5}$ Accu-check counting beads/mL (Life Technologies #PCB100). All samples were run on a Becton Dickinson X-20 Fortessa and absolute cell numbers for CARTs and Raji cells were calculated after acquiring 2000 beads.

Figure 7B:
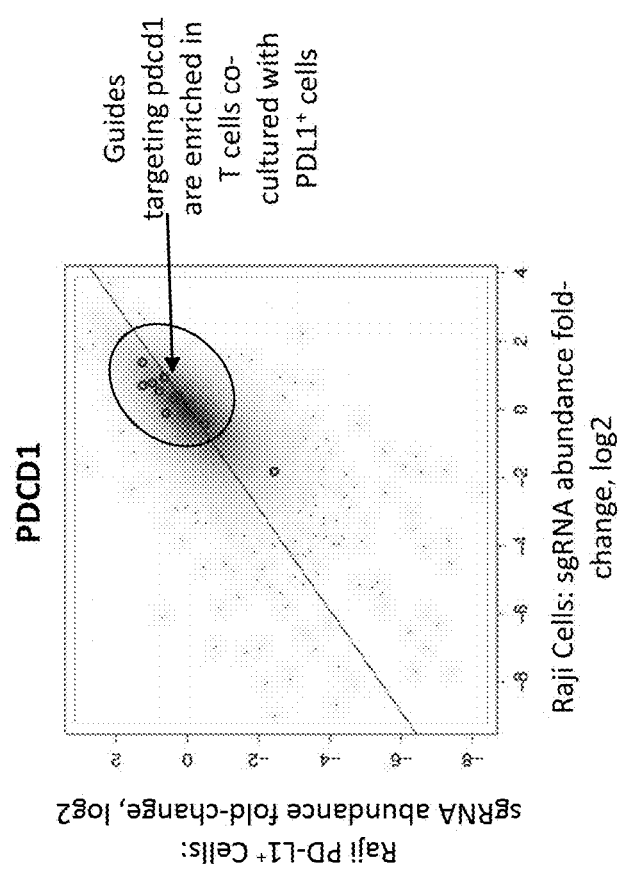

FIG. 7A shows the accumulation of T cells co-cultured with either PD-L1$^+$ or PD-L1$^-$ Raji cells over time. At the end of the experiment, CARTs were harvested, and distribution of guides determined by PCR amplification and next-generation sequencing (NGS) of guide RNAs. FIG. 7B shows the change in sgRNA abundance in CARTs cultured with PDL1$^+$ and parental Raji cells. Guides targeting the PD1 gene (PDCD1) were differentially enriched in CARTs cultured with Raji PD-L1$^+$ cells versus parental Raji cells (FIG. 7B).

Example 7: An In Vivo Screen Demonstrating Feasibility of the CRISPRT System

In vivo screens demonstrating the feasibility of the CRISPRT system in disseminated (FIG. 8A) and subcutaneous (FIG. 8B) cancer models were established. Both the disseminated and subcutaneous models used female Nod/scid/gamma (NSG) mice (NOD.Cg-Prkdc<scid>Il2rg<tm1Wjl>/SzJ; Stock number: 005557; Jackson Labs), which lack endogenous lymphocytes (e.g., T cells, B cells, and NK cells).

Disseminated Cancer Model

The Raji-Luciferase (Raji) cell line was acquired from Genscript (Sample ID C01X01), and express firefly luciferase allowing tracking engraftment of the tumors into mice. Raji-Luciferase cells were grown in suspension at 37° C. and 5% $CO_2$ in RPMI1640 supplemented with 10% FBS and passaged regularly to maintain a cell density less than 0.5×10$^6$ cells/mL of culture media. Prior to inoculation, cells were re-suspended at 1×10$^6$ viable cells/mL in PBS. Twenty, 7 week old female NSG mice were injected intravenously (i.v.) with 200 µL of the prepared Raji-Luciferase cell suspension into the lateral tail veins of warmed mice. Animals were monitored for engraftment by IVIS whole body luminescence imaging on Days 7, 10 and 14 post-injection. On each imaging day, twelve minutes prior to imaging, mice were injected with 150 mg/kg Rediject luciferin (Perkin Elmer. Cat #: 770504 Lot: UJ08RV01, Exp: 7-MAR 2018) intraperitoneally (i.p.) at a 5 mL/kg dose volume. Mice were subsequently anesthetized with isoflurane and imaged in the IVIS imager. Engraftment of Raji-Luciferase cells was tracked as the amount of flux (photons per second) detected by the IVIS imager.

On Day 7, following imaging, Raji-Luciferase engrafted mice were divided into three groups of 5 mice/group, receiving either PBS control or i.v. injections of Cas9-edited CD19 CART cells comprising an sgRNA library targeting ~6,000 genes with 10 guides/gene (generated as described in Example 1 and shown in FIG. 3). Group 1 received an injection of PBS to monitor normal progression of disseminated disease; Group 2 received 3×10$^6$ viable CAR T cells; and Group 3 received 6×10$^6$ CD19 CARTs per mouse and were monitored for progression of disseminated disease. Mice were euthanized on Day 14 after Raji-Luciferase inoculation (day 7 post CD19 CART treatment). Body weight was measured at least twice per week and mice were monitored for clinical symptoms of disease such as paralysis. At study end, spleen, whole blood and de-bulked femur and tibia were collected and snap frozen on liquid nitrogen and stored at −80° C. until processing to yield genomic DNA for guide sequencing.

Figure 8A:
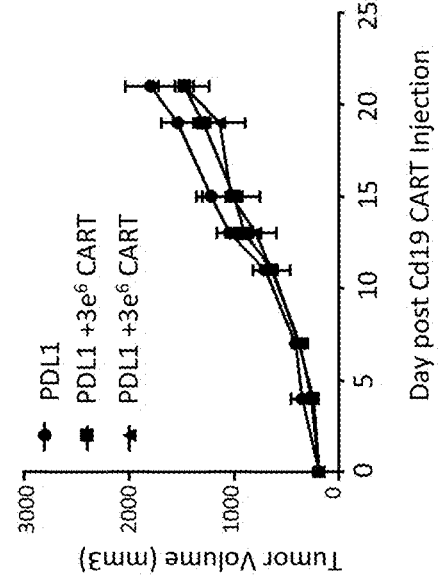
FIG. 8A shows growth curves of Raji-luciferase cells in a disseminated lymphoma model using immune-deficient NSG mice and CD19-specific CAR-T cells engineered to lack an endogenous TCR and containing a guide library targeting ~6,000 genes with 10 guides per genes.

FIG. 8A shows growth curves of Raji-luciferase cells growing in immune-deficient NSG mice in the presence of CD19-specific CAR-T cells engineered to lack an endogenous TCR and containing a guide library.

Subcutaneous Cancer Model

The colorectal cancer cell line DLD1 was purchased from ATCC, and engineered to express tCD19 (DLD1-tCD19) or tCD19 and PDL1 (DLD1-tCD19-PDL1) on the cell surface, as described in Example 3 and shown in in FIG. 4B. Cell lines were grown as an adherent cell line in RPMI640 supplemented with 10% FBS. For subcutaneous inoculation, cells were harvested, counted for viability, and re-suspended in ice cold PBS at a viable cell concentration of 10×10$^6$ viable cells/mL. This cell preparation was mixed with an equal volume of Matrigel (Corning Cat. 354234, Lot, 7009618) to yield a cell inoculum of 1×10$^6$ cells per 200 µL, which was injected subcutaneously into sixty female NSG mice. Each animal's body weight and tumor volume were measured at least twice per week. Tumor growth was monitored by caliper measurement of the longest perpendicular tumor diameters using the formula: (length (mm)× width$^2$ (mm))/2.

Mice injected with DLD1-tCD19 cells with tumor volumes between 167.5 mm$^3$ and 269.9 mm$^3$ and mice injected with DLD1-tCD19-PDL1 cells with tumor volumes between 156.8 mm$^3$ and 261.5 mm$^3$ were enrolled in the study. Mice were randomized based upon tumor volume and divided into treatment groups of 5 mice/group. Following randomization mice were treated with either PBS or CD19 CAR T cells again engineered to lack an endogenous TCR and containing a guide library targeting ~6,000 genes with 10 guides/gene (as described in Example 1 and shown in FIG. 3). Mice injected with DLD1-tCD19-PDL1 cells were treated with 3×10$^6$ CD19 CAR T cells or with 10×10$^6$ CD19 CAR T cells. The study endpoint was at day 21 post-CAR T injection and spleen, whole blood, and tumors were collected and snap frozen on liquid nitrogen and stored at −80° C. until processing to yield genomic DNA for guide sequencing.

Figure 8B:
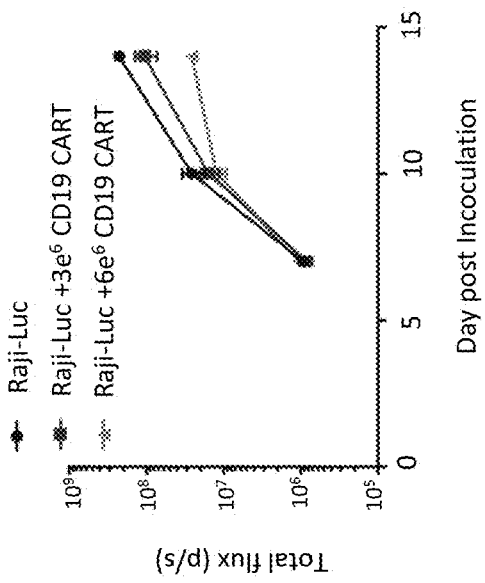
FIG. 8B shows growth curves of DLD1-tCD19-PDL1 cells in a subcutaneous lymphoma model using immune-deficient NSG mice and CD19-specific CAR-T cells engineered to lack an endogenous TCR and containing a guide library targeting ~6,000 genes with 10 guides per genes.

FIG. 8B shows growth curves of DLD1-tCD19-PDL1 cells growing subcutaneously in immune-deficient NSG mice in the presence of CD19-specific CAR-T cells.

The invention claimed is:
1. A method for obtaining T cells that are resistant to tumor suppression or deactivation, said method comprising:

(a) obtaining a population of tumor cells that are engineered to express an extracellular protein target;
(b) obtaining a primary cell population of T cells that are engineered to express:
  (i) a chimeric antigen receptor (CAR), said CAR comprising an intracellular signaling domain and an extracellular target-binding domain that binds to the extracellular protein target expressed by the population of tumor cells of (a), to form a population of CAR-T cells that express the extracellular target-binding domain on the cell surface, and
  (ii) a Cas9 protein and a gRNA library that selectively edit the CAR-T cells at one or more locations of the CAR-T cell genome to form a subpopulation of edited CAR-T cells;
(c) co-culturing the subpopulation of edited CAR-T cells of (b) with the population of tumor cells of (a); and
(d) isolating the edited CAR-T cells that accumulate over the co-culture period, wherein the isolated CAR-T cells have been edited in a manner as to make the CAR-T cells resistant to tumor suppression or deactivation, thereby obtaining T cells that are resistant to tumor suppression or deactivation.

2. The method of claim 1 wherein the subpopulation of edited CAR-T cells and the population of tumor cells are co-cultured for at least 7 days.

3. The method of claim 1 wherein said CAR-T cells have been engineered with a nucleic acid encoding the Cas9 protein.

4. The method of claim 3, wherein the nucleic acid encoding the Cas9 protein is mRNA and is introduced via electroporation.

5. The method of claim 3, wherein the nucleic acid encoding the Cas9 protein is encoded by a viral vector.

6. The method of claim 5, wherein the viral vector is a lentiviral vector and is introduced at a titer of at least about $1\times10^6$ infectious particles/mL.

7. The method of claim 1, wherein the Cas9 protein is a dCas9.

8. The method of claim 7, wherein the dCas9 is fused with a repressor domain.

9. The method of claim 8, wherein the repressor domain is selected from the group consisting of MAX-interacting protein 1 (MXI1), Krüppel-associated box (KRAB) domain and four concatenated mSin3 domains (SID4X).

10. The method of claim 7, wherein the dCas9 is fused with a transcriptional activator.

11. The method of claim 10, wherein the transcriptional activator is selected from the group consisting of (i) one or multiple repeats of the herpes simplex VP16 activation domain selected from the group consisting of VP64 and VP160, and (ii) the nuclear factor-κB (NF-κB) transactivating subunit activation domain p65AD.

12. The method of claim 11, wherein the Cas9 protein comprises a dCas9-VP64 fusion protein.

13. The method of claim 3, wherein the nucleic acid encoding the Cas9 protein further encodes a selectable marker.

14. The method of claim 13, wherein the selectable marker is a fluorophore or an antibiotic resistance gene.

15. A method for obtaining NK cells or NKT cells that are resistant to tumor suppression or deactivation, said method comprising:
(a) obtaining a population of tumor cells that are engineered to express an extracellular protein target;
(b) obtaining a primary cell population of NK cells or NKT cells that are engineered to express:
  (i) a chimeric antigen receptor (CAR), said CAR comprising an intracellular signaling domain and an extracellular target-binding domain that binds to the extracellular protein target expressed by the population of tumor cells of (a), to form a population of CAR-NK cells or CAR-NKT cells that express the extracellular target-binding domain on the cell surface, and
  (ii) a Cas9 protein and a gRNA library that selectively edit the CAR-NK cells or CAR-NKT cells in one or more locations of the CAR-NK cell genome or CAR-NKT cell genome to form a subpopulation of edited CAR-NK cells or edited CAR-NKT cells;
(c) co-culturing the subpopulation of edited CAR-NK cells or edited CAR-NKT cells of (b) with the population of tumor cells of (a);
(d) isolating the edited CAR-NK cells or edited CAR-NKT cells that accumulate over the co-culture period; wherein the isolated CAR-NK cells or CAR-NKT cells have been edited in a manner as to make said cells resistant to suppression or deactivation by said tumor, thereby obtaining NK cells or NKT cells that are resistant to tumor suppression or deactivation.

16. The method of claim 1, wherein the extracellular protein target is selected from the group consisting of HER2, EGFR, ERBB2, ERBB3, ERBB4, CD19, and CD20.

\* \* \* \* \*